United States Patent
Fleury et al.

(10) Patent No.: US 12,233,041 B2
(45) Date of Patent: Feb. 25, 2025

(54) DISULFONATE STILBENES FOR USE IN THE TREATMENT OF PROLIFERATIVE DISEASES

(71) Applicants: UNIVERSITÉ DE NANTES, Nantes (FR); CENTRE NATIONAL DE LA RECHERCHE SCIENTIFIQUE, Paris (FR); UNIVERSITÉ DU MANS, Le Mans (FR)

(72) Inventors: Fabrice Fleury, Orvault (FR); Alexandre Demeyer, Nantes (FR); Pierre Weigel, Orvault (FR); Benoit Chenais, Le Mans (FR); Monique Mathé, Nantes (FR); Jacques Lebreton, Nantes (FR)

(73) Assignees: UNIVERSITÉ DE NANTES, Nantes (FR); CENTRE NATIONAL DE LA RECHERCHE SCIENTIFIQUE, Paris (FR); UNIVERSITÉ DU MANS, Le Mans (FR)

(*) Notice: Subject to any disclaimer, the term of this patent is extended or adjusted under 35 U.S.C. 154(b) by 825 days.

(21) Appl. No.: 17/295,231
(22) PCT Filed: Nov. 22, 2019
(86) PCT No.: PCT/EP2019/082176
  § 371 (c)(1),
  (2) Date: May 19, 2021
(87) PCT Pub. No.: WO2020/104634
  PCT Pub. Date: May 28, 2020

(65) Prior Publication Data
  US 2022/0016068 A1   Jan. 20, 2022

(30) Foreign Application Priority Data
  Nov. 22, 2018   (EP) ..................................... 18306546

(51) Int. Cl.
  *A61K 31/27*   (2006.01)
  *A61K 31/166*  (2006.01)
  (Continued)

(52) U.S. Cl.
  CPC ............ *A61K 31/27* (2013.01); *A61K 31/166* (2013.01); *A61K 31/167* (2013.01); *A61K 31/18* (2013.01); *A61K 45/06* (2013.01)

(58) Field of Classification Search
  None
  See application file for complete search history.

(56) References Cited

U.S. PATENT DOCUMENTS

2013/0184342 A1*   7/2013   Mills ..................... C07C 311/08
                                                          514/516

FOREIGN PATENT DOCUMENTS

DE    3528992 A1    2/1987
EP    0 498 095 A1  8/1992
(Continued)

OTHER PUBLICATIONS

Brovelli et al., Nano Lett. 2008, 8, 12, 4546-4551 (Year: 2008).*
(Continued)

*Primary Examiner* — Jeffrey S Lundgren
*Assistant Examiner* — Anthony Joseph Seitz
(74) *Attorney, Agent, or Firm* — Maier & Maier, PLLC

(57) ABSTRACT

Compounds of general formula:

(Continued)

wherein $R^{OA}$ and $R^{OB}$ are independently selected from hydrogen and pharmaceutically acceptable cations; and $R^A$ and $R^B$ are identical and selected from amide, carbamate, sulphonamide, azido, cyano and halide. Also, a pharmaceutical composition including one of the compounds. The composition may also include another active ingredient, especially an antineoplastic agent. Further a compound or a composition for use as a medicament, especially a compound or a composition for use in the treatment of a proliferative disease such as for example cancer.

11 Claims, 5 Drawing Sheets

(51) Int. Cl.
*A61K 31/167* (2006.01)
*A61K 31/18* (2006.01)
*A61K 45/06* (2006.01)

(56) References Cited

FOREIGN PATENT DOCUMENTS

| WO | WO-9316992 A1 * | 9/1993 | ........... C07C 309/42 |
|---|---|---|---|
| WO | 00/58277 A1 | 10/2000 | |
| WO | 2010/148177 A2 | 12/2010 | |
| WO | 2013/003112 A1 | 1/2013 | |
| WO | 2016/094897 A1 | 6/2016 | |
| WO | 2017/031036 A1 | 2/2017 | |

OTHER PUBLICATIONS

International Search Report and Written Opinion issued on Feb. 26, 2020 in corresponding International Application No. PCT/EP2019/082176; 11 pages.
Jay Wrobel et al., "Synthesis of (bis)Sulfonic Acid, (bis)Benzamides as Follicle-Stimulating Hormone (FSH) Antagonists", Bioorganic & Medicinal Chemistry, vol. 10, 2002, pp. 639-656.
Fung-Min Zhou et al., "Knockdown of Chloride Channel-3 Inhibits Breast Cancer Growth In Vitro and In Vivo", Journal of Breast Cancer, vol. 21, No. 2, Jun. 2008, pp. 103-111.
Alagpulinsa, D. A. et al., "A small-molecule inhibitor of RAD51 reduces homologous recombination and sensitizes multiple myeloma cells to doxorubicin", Frontiers in Oncology, Oct. 2014, vol. 4, Article 289, pp. 1-11.
Goghari, M. H. et al., "Studies on Sulphonamides. Part V. Preparation, Antibacterial and Antifungal Activity of 4:4-Bis arylsulphonamidostilbene 2:2-disulphonic Acids", Journal of the Indian Chemical Society, Mar. 23, 1977, vol. 54, No. 6, pp. 621-622.
Huang, F. et al., "Inhibition of Homologous Recombination in Human Cells by Targeting RAD51 Recombinase", Journal of Medicinal Chemistry, Apr. 2012, vol. 55, pp. 3011-3020.
Ishida, T., et al., "DIDS, a chemical compound that inhibits RAD51-mediated homologous pairing and strand exchange", Nucleic Acids Research, Mar. 30, 2009, vol. 37, No. 10, pp. 3367-3376.
Jakobsen, P., et al., "Preparation and Characterization of 4-acetamido-4'-isothiocyanostilbene-2,2'-disulfonic Acid (SITS) and Related Stilbene Disulfonates", Stain Technology, 1989, vol. 64, No. 6, pp. 301-313.
Matulef, K., et al., "Discovery of Potent CLC Chloride Channel Inhibitors", ACS Chemical Biology, Jul. 18, 2008, vol. 3, No. 7, pp. 419-428.
Wilson, M. C., et al., Studies on the DIDS-binding Site of Monocarboxylate Transporter 1 Suggest a Homology Model of the Open Conformation and a Plausible Translocation Cycle, Journal of Biological Chemistry, May 27, 2009, vol. 284, No. 30, pp. 20011-20021.

* cited by examiner

DISULFONATE STILBENES FOR USE IN THE TREATMENT OF PROLIFERATIVE DISEASES

FIELD

The present invention relates to disulfonate stilbene compounds useful as inhibitors of RAD51 protein, especially to disulfonate stilbenes for use in the treatment of proliferative diseases.

BACKGROUND

Proliferative diseases therapies such as radiotherapy or chemotherapy often encounter induced and/or intrinsic resistance from cancer cells. DNA repair pathways are susceptible of restoring the DNA of cancer cells which were damaged by the treatment, thereby reducing the efficacy of said treatment. Inhibition of DNA repair pathways is thus an interesting option for sensitizing tumors to antineoplastic treatments.

Double-strand breaks (DSBs) are the most deleterious nucleic alterations of DNA and can be repaired by a biological process called homologous recombination (HR). RAD51 protein is the main element of HR repair pathway. The first step of RAD51 protein recombinase activity is the formation of a RAD51 protein nucleofilament which catalyses the homology search and the strand exchange between damaged DNA sequence and a homologous sequence, thereby ensuring the accurate repair of DSB. Thus, deregulation of RAD51 protein can lead to carcinogenesis and promote the resistance of cancers. The overexpression of RAD51 protein causes genomic instability of the cells at the origin of some cancers and also provides resistance by promoting the repair of DSBs induced by some anticancer treatments. Especially, it has been shown that the survival of patients treated for cancer and expressing a higher level of RAD51 protein is shorter and that a decrease in the amount of RAD51 protein by antisense or ribozyme treatment improves the effectiveness of cancer treatment by radiotherapy. Hence, RAD51 protein is a relevant biological target to modulate HR and thus achieves better potency of antiproliferative treatments.

The identification of small molecules exhibiting anti-recombinase activities has attracted increasing attention and several RAD51 protein inhibitory small molecules have been found. Those are able to interfere directly with certain steps of RAD51 protein recombinase activity and thereby to prevent or to limit the HR repair pathway. Examples of RAD51 protein small molecules inhibitors of the art are the following:

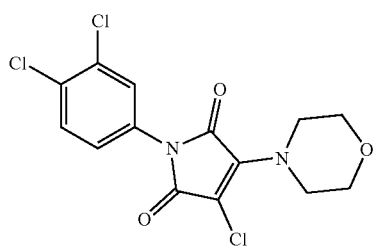

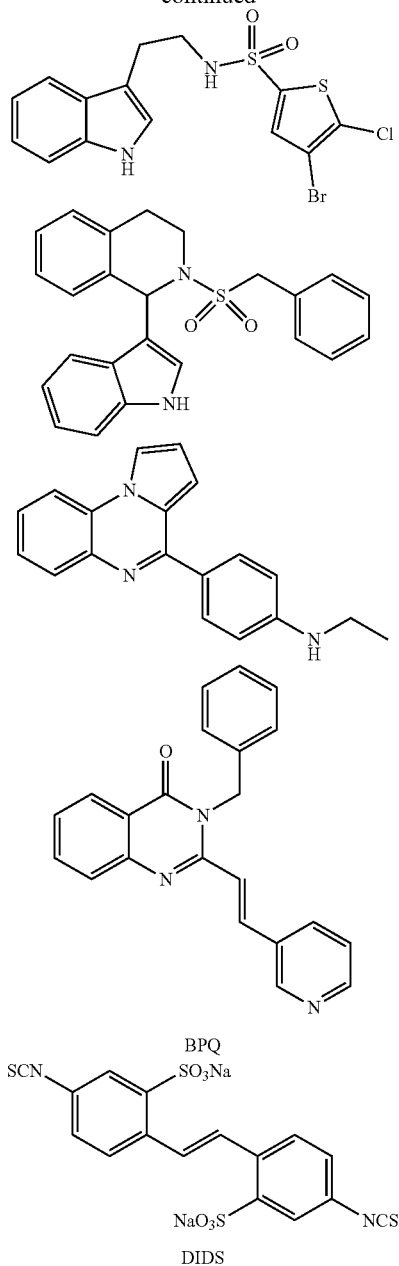

Especially, it was shown that BPQ impaired RAD51 filament formation by targeting protein-DNA interactions (Huang, F. et al., "Inhibition of Homologous Recombination in Human Cells by Targeting RAD51 Recombinase", *Journal of Medicinal Chemistry*, April 2012, Vol. 55, pp. 3011-3020) and that sensitization of cancer cells treated with doxorubicin could be observed (Alagpulinsa, D. A. et al., "A small-molecule inhibitor of RAD51 reduces homologous recombination and sensitizes multiple myeloma cells to doxorubicin", *Frontiers in Oncology*, October 2014, Vol. 4, p. 289).

Especially, it was shown that DIDS is able to inhibit RAD51 recombinase activity during HR (Ishida, T., et al., "DIDS, a chemical compound that inhibits RAD51-mediated homologous pairing and strand exchange.", *Nucleic Acids Research*, 2009, Vol. 37, No. 10, pp. 3367-3376). Although it seems that the inhibiting activity results from DIDS direct interaction with RAD51 protein, DIDS mechanism of action was not elucidate and the involved biological targets remain undetermined.

However, RAD51 protein small molecules inhibitors such as DIDS or BPQ suffer from limitations which impair their medical use against cancer regarding for example therapeutic efficiency (e.g., regarding the sensitizing effect), presence or potency of side-effects, selectivity over others biological receptors and/or chemical stability of the molecule.

Especially, DIDS as inhibitor is not specific of RAD51 protein because it also inhibits membrane transporters (Wilson, M. C., et al. "Studies on the DIDS-binding site of monocarboxylate transporter 1 suggest a homology model of the open conformation and a plausible translocation cycle.", *Journal of Biological Chemistry*, 2009, Vol. 284, No. 30, pp. 20011-20021) and ion channels (Matulef, K., et al. "Discovery of potent CLC chloride channel inhibitors.", *ACS Chemical Biology*, 2008, Vol. 3, No. 7, pp. 419-428). Hence, DIDS may induce deleterious side-effects such as cytotoxicity.

Moreover, the isothiocyanate function of DIDS is known to be sensitive to hydrolysis (Jakobsen, P. and Horobin, R. W., "Preparation and Characterization of 4-Acetamido-4'-Isothiocyanostilbene-2,2'-Disulfonic Acid (Sits) And Related Stilbene Disulfonates" *Stain Technology*, 1989, Vol. 64, No. 6, pp. 301-313) and consequently DIDS oligomers could be formed with potential chloride channel or transporters inhibition activity (see for example WO 2010/148177 A2).

The Applicant carried out in-depth research in order to conceive and synthetize novel RAD51 protein inhibitors susceptible in order to overcome the limitations of known compounds. During the course of this research, it was surprisingly found that some disulfonate stilbene compounds are potent inhibitors of RAD51 protein and may thus be useful in the treatment of proliferative diseases.

The disulfonate stilbenes according to the invention are potent RAD51 protein inhibitors. Their efficacy is comparable to or better than RAD51 inhibitors of the art. Especially, they efficiently sensitize proliferative cells in presence of an antineoplastic drug.

The disulfonate stilbenes according to the invention induce less deleterious side-effects than RAD51 inhibitors of the art. Especially, they have lower cytotoxicity.

The disulfonate stilbenes according to the invention may also have improved chemical stability compared to the molecules of the art.

SUMMARY

This invention relates to a compound of Formula (I)

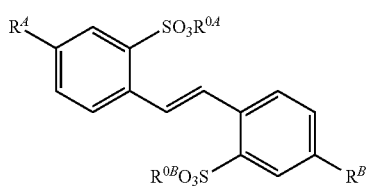

(I)

wherein
$R^{OA}$ and $R^{OB}$ are independently selected from hydrogen, lithium, sodium and potassium; and $R^A$ and $R^B$ are identical and selected from —NH—COR, —NH—COOR, —NH—SO$_2$R, azido, cyano and halide;
wherein each R is independently selected from (C$_1$-C$_6$)-alkyl, (C$_3$-C$_6$)-cycloalkyl, (C$_6$-C$_{10}$)-aryl and (C$_6$-C$_{10}$)-heteroaryl group;
the group being optionally substituted by one or two substituent(s) independently selected from (C$_1$-C$_6$)-alkyl, (C$_3$-C$_6$)-cycloalkyl, (C$_1$-C$_6$)-alkoxy, (C$_1$-C$_6$)-alkyl-S— and nitro;
or a pharmaceutically acceptable salt thereof;
for use in the treatment of a proliferative disease.

According to one embodiment, each R is independently selected from (C$_1$-C$_4$)-alkyl, phenyl, pyridinyl or diazinyl group; the phenyl, pyridinyl or diazinyl group being optionally substituted by one or two substituent(s) independently selected from (C$_1$-C$_3$)-alkyl, (C$_1$-C$_3$)-alkoxy and nitro, preferably selected from methyl, methoxy and nitro. According to one embodiment, $R^A$ and $R^B$ are selected from —NH—COR, —NH—COOR and —NH—SO$_2$R. According to one embodiment, $R^A$ and $R^B$ are selected from azido, cyano and halide. According to one embodiment, the halide is iodine. According to one embodiment, both $R^{OA}$ and $R^{OB}$ are sodium or both $R^{OA}$ and $R^{OB}$ are potassium.

According to one embodiment, the compound is selected from:
sodium (E)-6,6'-(ethene-1,2-diyl)bis(3-acetamidobenzenesulfonate);
sodium (E)-6,6'-(ethene-1,2-diyl)bis(3-propionamidobenzenesulfonate);
sodium (E)-6,6'-(ethene-1,2-diyl)bis(3-benzamidobenzenesulfonate);
sodium (E)-6,6'-(ethene-1,2-diyl)bis(3-(4-methoxybenzamido)benzenesulfonate);
sodium (E)-6,6'-(ethene-1,2-diyl)bis(3-(4-nitrobenzamido)benzenesulfonate);
sodium (E)-6,6'-(ethene-1,2-diyl)bis(3-((ethoxycarbonyl)amino)benzenesulfonate);
sodium (E)-6,6'-(ethene-1,2-diyl)bis(3-((isobutoxycarbonyl)amino)benzenesulfonate);
sodium (E)-6,6'-(ethene-1,2-diyl)bis(3-((phenoxycarbonyl)amino)benzenesulfonate);
sodium (E)-6,6'-(ethene-1,2-diyl)bis(3-(phenylsulfonamido)benzenesulfonate);
sodium (E)-6,6'-(ethene-1,2-diyl)bis(3-((4-methylphenyl)sulfonamido)benzenesulfonate);
sodium (E)-6,6'-(ethene-1,2-diyl)bis(3-((4-nitrophenyl)sulfonamido)benzenesulfonate);
sodium (E)-6,6'-(ethene-1,2-diyl)bis(3-azidobenzenesulfonate);
sodium (E)-6,6'-(ethene-1,2-diyl)bis(3-cyanobenzenesulfonate); and
potassium (E)-6,6'-(ethene-1,2-diyl)bis(3-iodobenzenesulfonate).

According to one embodiment, the proliferative disease is a cancer; preferably breast cancer, glioblastoma or multiple myeloma.

The invention also relates to a composition comprising a compound of Formula (I) for the use according to the invention and a pharmaceutically acceptable excipient.

According to one embodiment, the composition further comprises at least another active ingredient. In one embodiment, the at least another active ingredient is an antineoplastic active ingredient.

The invention also relates to a compound of Formula (II)

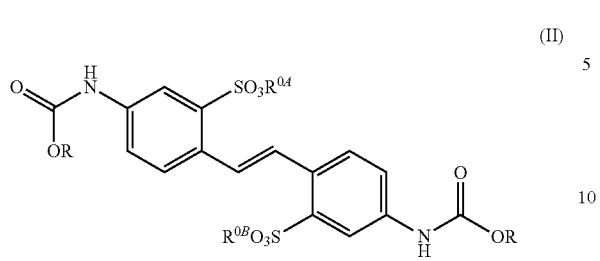

(II)

wherein
$R^{OA}$ and $R^{OB}$ are independently selected from hydrogen, lithium, sodium and potassium; and
each R is independently selected from $(C_6$-$C_{10})$-aryl and $(C_6$-$C_{10})$-heteroaryl group;
or a pharmaceutically acceptable salt thereof.

According to one embodiment, each R is independently selected from phenyl, pyridinyl and diazinyl; preferably phenyl. According to one embodiment, $R^{OA}$ and $R^{OB}$ are identical; preferably $R^{OA}$ and $R^{OB}$ are sodium.

The invention also relates to a process for manufacturing a compound of formula (II) according to the invention, comprising a step of reaction of (E)-6,6'-(ethene-1,2-diyl) bis(3-aminobenzenesulfonate) with an halo-formate.

DETAILED DESCRIPTION

Figure 1:
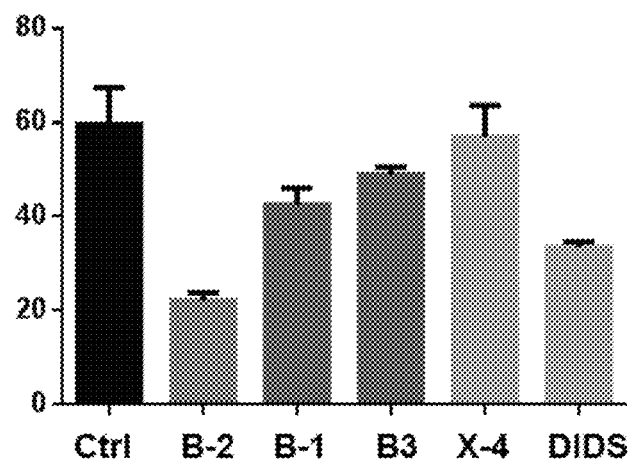
FIG. 1 is a series of histograms each showing on the y-axis the oligomerization degree of RAD51 protein in presence of one of compounds B-1 to B-3, X-4 and DIDS as presented in Example 2 below.

In the present invention, the following terms have the following meanings:

"Active ingredient" and "active pharmaceutical ingredient" and "therapeutic agent" refer to a compound for therapeutic use and relating to health. Especially, an active ingredient may be indicated for treating or preventing a disease, preferably a proliferative disease. An active ingredient may also be indicated for improving the therapeutic activity of another active ingredient for treating or preventing a disease, preferably a proliferative disease.

"Alkene" or "alkenyl" refer to any linear or branched hydrocarbon chain with 2 to 12 carbon atoms, preferably 2 to 8 carbon atoms, more preferably 1 to 6 carbon atoms, furthermore preferably 1 to 4 carbon atoms; having at least one double bond. Examples of alkenyl groups are ethenyl, 2-propenyl, 2-butenyl, 3-butenyl, 2-pentenyl and its isomers, 2-hexenyl and its isomers, or 2,4-pentadienyl.

"Alkoxy" refers to a group of formula —O-alkyl.

"Alkyl" refers to any saturated linear or branched hydrocarbon chain with 1 to 12 carbon atoms, preferably 1 to 8 carbon atoms, more preferably 1 to 6 carbon atoms, furthermore preferably 1 to 4 carbon atoms. Examples of alkyl groups are methyl, ethyl, n-propyl, i-propyl, n-butyl, i-butyl, s-butyl, t-butyl, pentyl and its isomers (e.g. n-pentyl or i-pentyl), or hexyl and its isomers (e.g., n-hexyl or i-hexyl).

"Alkyne" or "alkynyl" refer to any linear or branched hydrocarbon chain with 2 to 12 carbon atoms, preferably 2 to 8 carbon atoms, more preferably 1 to 6 carbon atoms, furthermore preferably 1 to 4 carbon atoms; having at least one triple bond. Examples of alkynyl groups are ethynyl, 2-propynyl, 2-butynyl, 3-butynyl, 2-pentynyl and its isomers, or 2-hexynyl and its isomers.

"Amide" refers to a group comprising the amide moiety (—NH—CO—).

"Aryl" refers to a polyunsaturated, aromatic hydrocarbon group with 5 to 16 carbon atoms, preferably 6 to 12 carbon atoms, more preferably 6 to 10 carbon atoms; having a single ring (i.e., phenyl) or multiple aromatic rings fused together (e.g., naphtyl) or linked covalently, wherein at least one ring is aromatic. The aromatic ring may optionally include one to two additional rings (either cycloalkyl, heterocyclyl or heteroaryl) fused thereto. Examples of aryl are phenyl, biphenylyl, biphenylenyl, 5- or 6-tetralinyl, naphthalen-1- or -2-yl, 4-, 5-, 6 or 7-indenyl, 1-2-, 3-, 4- or 5-acenaphtylenyl, 3-, 4- or 5-acenaphtenyl, 1- or 2-pentalenyl, 4- or 5-indanyl, 5-, 6-, 7- or 8-tetrahydronaphthyl, 1,2,3,4-tetrahydronaphthyl, 1,4-dihydronaphthyl, 1-, 2-, 3-, 4- or 5-pyrenyl.

"Azido" refers to a group of formula —$N_3$.

"BPQ" refers to (E)-3-benzyl-2-(2-(pyridin-3-yl)vinyl) quinazolin-4(3H)-one.

"Carbamate" refers to a group comprising the carbamate moiety (—NH—COO—).

"Ctrl" means "control".

"Cyano" refers to a group of formula —CN.

"Cycloalkyl" refers to any cyclic or polycyclic alkyl group comprising at least 3 carbon atoms, linear or branched. Examples of cycloalkyl groups are cyclopropyl, cyclopentyl or cyclohexyl.

"Cycloalkenyl" refers to any cyclic or polycyclic alkenyl group comprising at least 5 carbon atoms, linear or branched.

"DIDS" refers to 4,4'-Diisothiocyano-2,2'-stilbene disulfonic acid.

"Disease" encompasses any disease, disorder or condition, preferably a proliferative disease, disorder or condition. The aim of a treatment is to prevent or slow down a disease in a subject in need thereof.

"DNA" refers to deoxyribonucleic acid.

"Halide" refers to a fluorine (F), chlorine (Cl), bromine (Br) or iodine (I) atom.

"Heteroaryl" refers to aromatic rings or aromatic ring systems with 5 to 16 carbon atoms, preferably 6 to 12 carbon atoms, more preferably 6 to 10 carbon atoms; having one or two rings which are fused together or linked covalently, wherein at least one ring is aromatic; and wherein one or more carbon atoms in one or more of these rings is replaced by oxygen, nitrogen and/or sulfur atoms, wherein the nitrogen and sulfur heteroatoms may optionally be oxidized and the nitrogen heteroatoms may optionally be quaternized. Such rings may be fused to an aryl, cycloalkyl, heteroaryl or heterocyclyl ring. Examples of heteroaryl are furanyl, thiophenyl, pyrazolyl, imidazolyl, oxazolyl, isoxazolyl, thiazolyl, isothiazolyl, triazolyl, oxadiazolyl, thiadiazolyl, tetrazolyl, oxatriazolyl, thiatriazolyl, pyridinyl, pyrimidyl, pyrazinyl, pyridazinyl, oxazinyl, dioxinyl, thiazinyl, triazinyl, imidazo[2, 1-b] [1,3] thiazolyl or thieno [3,2-b] furanyl.

"Heteroalkyl" refers to any alkyl group comprising at least 3 carbon atoms and which is interrupted by at least one heteroatom selected from oxygen, nitrogen and sulfur. The nitrogen and sulfur heteroatoms may optionally be oxidized and the nitrogen heteroatoms may optionally be quaternized.

"Heterocycloalkyl" refers to any non-aromatic cyclic or polycyclic alkyl group comprising at least 3 carbon atoms, linear or branched, which is interrupted by at least one heteroatom selected from oxygen, nitrogen and sulfur. The nitrogen and sulfur heteroatoms may optionally be oxidized and the nitrogen heteroatoms may optionally be quaternized.

"Nitro" refers to a group of formula —$NO_2$.

"Pharmaceutical composition" refers to a composition comprising an active ingredient in association with a pharmaceutically acceptable excipient. A pharmaceutical composition is for therapeutic use and relates to health. Especially, a pharmaceutical composition may be indicated for treating or preventing a disease, preferably a proliferative disease.

"Pharmaceutically acceptable" means that the ingredients of a pharmaceutical composition are compatible with each other and not deleterious when administered to a subject.

"Pharmaceutically acceptable excipient" refers to an excipient or vehicle that does not produce an adverse, allergic or other untoward reaction when administered to a subject. It includes any and all solvents, dispersion media, coatings, antibacterial and antifungal agents, isotonic and absorption delaying agents, and the like. For human administration, preparations should meet sterility, pyrogenicity, general safety and purity standards as required by regulatory offices, such as, for example, Food and Drug Administration (FDA) or European Medicine Agency (EMA).

"RAD51", "RAD51A" or "RECA" refers to RAD51 gene.

"RAD51 protein" as shortcut for "DNA repair protein RAD51 homolog 1" or "RAD51 recombinase" refers to the protein encoded by RAD51.

"RAD51 protein nucleofilament" refers to the pre-synaptic filament assembly which is involved in the major step of the RAD51 protein-dependent homologous recombination (HR) process (Velic, D. et al., "DNA Damage Signalling and Repair Inhibitors", *Biomolecules*, November 2015, Vol. 5, No. 4, pp. 3204-3059).

"Subject" refers to a warm-blooded animal, preferably a mammal, more preferably a human. Preferably, the subject is a patient, i.e., a subject who is awaiting the receipt of, or who is receiving medical care, or who is/will be the object of a medical procedure. Preferably, the subject has a proliferative disease.

"Sulphonamide" refers to a group comprising the sulphonamide moiety (—NH—$SO_2$—).

"Treating" or "treatment" or "alleviation" refers to both therapeutic treatment and prophylactic or preventative measures; wherein the object is to prevent or slow down (lessen) the targeted disease in a subject in need thereof. Those in need of treatment include those already with the disease, disorder or condition as well as those prone to have the disorder or those in whom the disorder is to be prevented. A subject is successfully "treated" for a disease, disorder or condition if, after receiving a therapeutic amount of an substance or composition according to the present invention, the subject shows observable and/or measurable reduction in or absence of one or more of the following: reduction in the number of pathogenic cells; reduction in the percent of total cells that are pathogenic; relief to some extent, of one or more of the symptoms associated with the specific disease, disorder or condition; reduced morbidity and mortality; and/or improvement in quality of life issues. The above parameters for assessing successful treatment and improvement in the disease, disorder or condition are readily measurable by routine procedures familiar to a physician. Preferably, the disease to be treated is a proliferative disease.

Where chemical substituents are combinations of chemical groups, the point of attachment of the substituent to the molecule is by the last chemical group recited. For example, an "arylalkyl" substituent is linked to the rest of the molecule through the alkyl moiety and it may be represented as follows: "aryl-alkyl-".

Compounds

This invention relates to a compound of Formula (I-0)

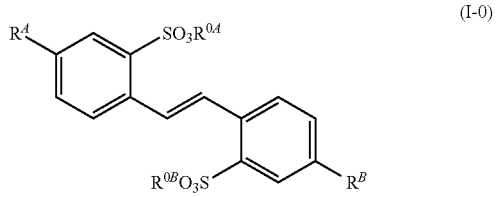

wherein
$R^{OA}$ and $R^{OB}$ are independently selected from hydrogen; pharmaceutically acceptable cations; and sulfonate function protecting groups or precursors; and
$R^A$ and $R^B$ are independently selected from amide, carbamate, sulphonamide, azido, cyano and halide.

According to one embodiment, $R^A$ and $R^B$ are identical. In one embodiment, $R^A$ and $R^B$ are the same amide. In one embodiment, $R^A$ and $R^B$ are the same carbamide. In one embodiment, $R^A$ and $R^B$ are the same sulphonamide. In one embodiment, $R^A$ and $R^B$ are azido. In one embodiment, $R^A$ and $R^B$ are cyano. In one embodiment, $R^A$ and $R^B$ are halide.

According to one embodiment, $R^A$ and $R^B$ are independently selected from amide, carbamate and sulphonamide. According to one embodiment, the amide is —NH—COR; the carbamate is —NH—COOR; and/or the sulphonamide is —NH—SO$_2$R;

wherein each R is independently selected from alkyl, arylalkyl, heteroarylalkyl, cycloalkyl, arylcycloalkyl, heteroarylcycloalkyl, alkenyl, arylalkenyl, heteroarylalkenyl, cycloalkenyl, arylcycloalkenyl, heteroarylcycloalkenyl, alkynyl, arylalkynyl, heteroarylalkynyl, aryl, alkylaryl, cycloalkylaryl, alkenylaryl, cycloalkenylaryl, alkynylaryl, heteroaryl, alkylheteroaryl, cycloalkylheteroaryl, alkenylheteroaryl, cycloalkenylheteroaryl and alkynylheteroaryl group;

wherein the group or the substituent is optionally interrupted by at least one heteroatom selected from oxygen (O), nitrogen (N) and sulfur (S);

the group is optionally substituted by at least one substituent selected from alkyl, cycloalkyl, alkenyl, cycloalkenyl, alkynyl, aryl, heteroaryl, amino (—NH$_2$), azido (—N$_3$), cyano (—CN), nitro (—NO$_2$), oxo (=O), halide, hydroxyl (—OH), formyl (—C(O)H), carboxyl (—COOH), amido (—C(O)—NH$_2$) and thio (=S) and sulfhydryl (—SH);

the nitrogen or sulfur atoms substituting or comprised in the group or in the substituent are optionally oxidized, and the nitrogen atoms substituting or comprised in the group or in the substituent are optionally quaternized.

In one embodiment, R is selected from alkyl, cycloalkyl, heteroalkyl, heterocycloalkyl, aryl and heteroaryl group; wherein the group is optionally interrupted, substituted, oxidized and/or quaternized as described hereabove. In one specific embodiment, R is selected from alkyl, cycloalkyl, aryl and heteroaryl group; wherein the group is optionally interrupted, substituted, oxidized and/or quaternized as described hereabove. In one further specific embodiment, R is selected from ($C_1$-$C_6$)-alkyl ($C_3$-$C_6$)-cycloalkyl, ($C_6$-$C_{10}$)-aryl and ($C_6$-$C_{10}$)-heteroaryl group; wherein the group is optionally interrupted, substituted, oxidized and/or quaternized as described hereabove. In one further specific embodiment, R is selected from alkyl and aryl group; wherein the group is optionally interrupted, substituted, oxidized and/or quaternized as described hereabove. In one further specific embodiment, R is selected from alkyl and cycloalkyl group; wherein the group is optionally interrupted, substituted, oxidized and/or quaternized as described hereabove. In one further specific embodiment, R is selected from aryl and heteroaryl group; wherein the group is optionally interrupted, substituted, oxidized and/or quaternized as described hereabove.

In one embodiment, R is selected from the groups as defined hereabove; wherein the group is optionally interrupted, oxidized or quaternized as described hereabove; and wherein the group is optionally substituted by at least one substituent selected from alkyl, cycloalkyl, alkoxy, alkyl-S— and nitro. In one specific embodiment, R is selected from the groups as defined hereabove; wherein the group is optionally interrupted, oxidized or quaternized as described hereabove; and wherein the group is optionally substituted by at least one substituent selected from ($C_1$-$C_6$)-alkyl, ($C_3$-$C_6$)-cycloalkyl, ($C_1$-$C_6$)-alkoxy, ($C_1$-$C_6$)-alkyl-S— and nitro; preferably selected from ($C_1$-$C_3$)-alkyl, ($C_1$-$C_3$)-alkoxy and nitro; more preferably selected from ($C_1$-$C_2$)-alkyl, ($C_1$-$C_2$)-alkoxy and nitro; further more preferably selected from methyl, methoxy and nitro. In one specific embodiment, R is selected from the groups as defined hereabove; wherein the group is optionally interrupted, oxidized or quaternized as described hereabove; and wherein the group is optionally substituted by at least one substituent selected from alkyl, alkoxy and nitro. In one embodiment, R is selected from the groups as defined hereabove; wherein the group is optionally interrupted, oxidized or quaternized as described hereabove; and wherein the group is optionally substituted by at least one substituent selected from ($C_1$-$C_3$)-alkyl, ($C_1$-$C_3$)-alkoxy and nitro; preferably selected from ($C_1$-$C_2$)-alkyl, ($C_1$-$C_2$)-alkoxy and nitro; more preferably selected from methyl, methoxy and nitro.

In one more specific embodiment, R is selected from alkyl, cycloalkyl, aryl and heteroaryl group; the group being optionally substituted by at least one substituent selected from alkyl, cycloalkyl, alkoxy, alkyl-S— and nitro. In one furthermore specific embodiment, R is selected from alkyl and aryl group; the aryl group being optionally substituted by at least one substituent selected from alkyl, alkoxy and nitro. For example, R as alkyl may be methyl, ethyl, propyl and butyl. For example, R as aryl may be phenyl without substituent or phenyl substituted by exactly one group selected from methyl, methoxy and nitro.

In one more specific embodiment, R is ($C_1$-$C_4$)-alkyl such as methyl, ethyl, propyl (such as n-propyl and iso-propyl) and butyl (such as n-butyl, iso-butyl and tert-butyl).

In another more specific embodiment, R is phenyl; wherein the phenyl is optionally interrupted, substituted, oxidized and/or quaternized as described hereabove.

In another more specific embodiment, R is pyridinyl or diazinyl; wherein the pyridinyl or diazinyl is optionally interrupted, substituted, oxidized and/or quaternized as described hereabove. Pyridinyl or diazinyl groups may be bond to amide, carbamate or sulphonamide function either by a carbon atom (e.g., 2-pyridinyl, 3-pyridinyl, 4-pyridinyl, 5-pyridinyl or 6-pyridinyl) or nitrogen atom (e.g., 1-pyridinyl) of the pyridinyl or diazinyl; preferably by a carbon atom of the pyridinyl or diazinyl.

In one embodiment, R is substituted by one or two substituent(s) as described hereinabove. In one specific embodiment, R is substituted by exactly one substituent as described hereinabove.

According to one embodiment, $R^A$ and $R^B$ are independently selected from azido, cyano and halide. In one embodiment, the halide is iodine (I) atom.

According to one embodiment, at least one among $R^A$ and $R^B$ is not an amide, especially is not —NH—COR, wherein R is as described hereinabove. In one embodiment, both $R^A$ and $R^B$ are not an amide. According to one embodiment, at least one among $R^A$ and $R^B$ is not a sulphonamide, especially is not —NH—SO$_2$R, wherein R is as described hereinabove. In one embodiment, both $R^A$ and $R^B$ are not a sulphonamide. According to one embodiment, at least one among R groups is not an alkyl. In one embodiment, no R group is an alkyl. According to one embodiment, at least one among R groups is not a cycloalkyl. In one embodiment, no R group is a cycloalkyl. According to one embodiment, at least one among R groups is not substituted by a sulfonate function (—SO$_2$—). In one embodiment, no R group is substituted by a sulfonate function.

According to one embodiment, $R^{OA}$ and $R^{OB}$ are identical. In one embodiment, $R^{OA}$ and $R^{OB}$ are hydrogen. In one embodiment, $R^{OA}$ and $R^{OB}$ are the same pharmaceutically acceptable cation.

According to one embodiment, $R^{OA}$ and/or $R^{OB}$ is a pharmaceutically acceptable alkaline cation. In one embodiment, the pharmaceutically acceptable alkaline cation is selected from lithium (Li$^+$), sodium (Na$^+$) and potassium (K$^+$). Preferably, the pharmaceutically acceptable alkaline cation is sodium (Na$^+$) or potassium (K+), more preferably sodium (Na+).

According to one embodiment, $R^{OA}$ and/or $R^{OB}$ is an alkyl group as described hereinabove, such as for example ethyl, iso-pentyle, methyl, ethyl, isopropyl or neopentyl. In this embodiment, the compound of Formula (I-0) is useful for example as a synthetic precursor.

According to one embodiment, $R^{OA}$ and/or $R^{OB}$ is an aryl group as described hereinabove, such as for example phenyl or para-nitrophenyl. In one embodiment, the alkyl group is selected from ethyl. In this embodiment, the compound of Formula (I-0) is useful for example as a prodrug.

According to one embodiment, $R^{OA}$ and/or $R^{OB}$ is a group comprising a function that can be converted by enzymatic systems (e.g. nitro-reductases or esterases) into the free sulfonate function, such as the functions disclosed in WO 2011/017800 A1 (Kong, X. et al.). In this embodiment, the compound of Formula (I-0) is useful for example as a prodrug.

According to one embodiment, the compound according to the invention is a compound of Formula (I-a)

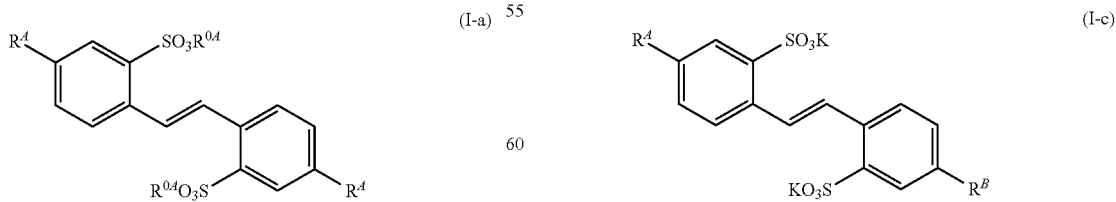

(I-a)

wherein $R^{AO}$ and $R^A$ are as described hereabove.

In one embodiment, the compound according to the invention is a compound of Formula (I-a-i)

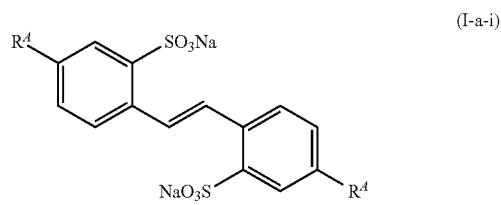

(I-a-i)

wherein $R^A$ is as described hereabove.

In one embodiment, the compound according to the invention is a compound of Formula (I-a-ii)

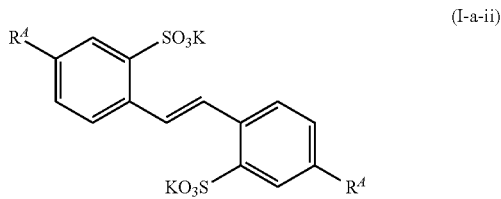

(I-a-ii)

wherein $R^A$ is as described hereabove.

According to one embodiment, the compound according to the invention is a compound of Formula (I-b)

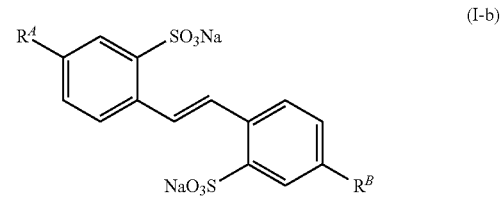

(I-b)

wherein $R^A$ and $R^B$ are as described hereabove.

According to one embodiment, the compound according to the invention is a compound of Formula (I-c)

(I-c)

wherein $R^A$ and $R^B$ are as described hereabove.

According to one embodiment, the compound according to the invention is a compound of Formula (II-0)

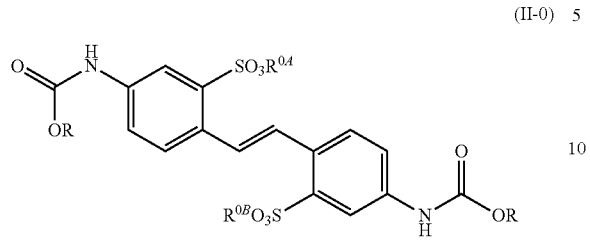

(II-0)

wherein $R^A$ and $R^B$ and each R are as described hereabove.

According to one embodiment, the compound according to the invention is a compound of Formula (III-0)

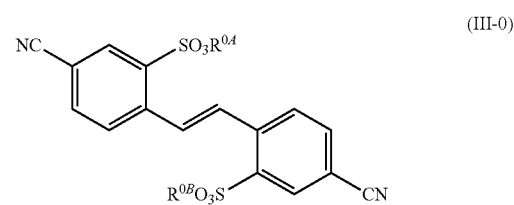

(III-0)

wherein $R^A$ and $R^B$ are as described hereabove.

In one specific embodiment, the compound according to the invention is selected from the compounds of Table 1 below:

TABLE 1

| # | Formula | Name |
|---|---------|------|
| A-1 | | sodium (E)-6,6'-(ethene-1,2-diyl)bis(3-acetamidobenzenesulfonate) |
| A-2 | | sodium (E)-6,6'-(ethene-1,2-diyl)bis(3-propionamidobenzenesulfonate) |
| A-3 | | sodium (E)-6,6'-(ethene-1,2-diyl)bis(3-benzamidobenzenesulfonate) |
| A-4 | | sodium (E)-6,6'-(ethene-1,2-diyl)bis(3-(4-methoxybenzamido)benzenesulfonate) |

TABLE 1-continued

| # | Formula | Name |
|---|---|---|
| A-5 | | sodium (E)-6,6'-(ethene-1,2-diyl)bis(3-(4-nitrobenzamido)benzenesulfonate) |
| C-1 | | sodium (E)-6,6'-(ethene-1,2-diyl)bis(3-((ethoxycarbonyl)amino)benzenesulfonate) |
| C-2 | | sodium (E)-6,6'-(ethene-1,2-diyl)bis(3-((isobutoxycarbonyl)amino)benzenesulfonate) |
| C-3 | | sodium (E)-6,6'-(ethene-1,2-diyl)bis(3-((phenoxycarbonyl)amino)benzenesulfonate) |
| S-1 | | sodium (E)-6,6'-(ethene-1,2-diyl)bis(3-(phenylsulfonamido)benzenesulfonate) |
| S-2 | | sodium (E)-6,6'-(ethene-1,2-diyl)bis(3-((4-methylphenyl)sulfonamido)benzenesulfonate) |

TABLE 1-continued

| # | Formula | Name |
|---|---|---|
| S-3 | | sodium (E)-6,6'-(ethene-1,2-diyl)bis(3-((4-nitrophenyl)sulfonamido)benzenesulfonate) |
| B-1 | | sodium (E)-6,6'-(ethene-1,2-diyl)bis(3-azidobenzenesulfonate) |
| B-2 | | sodium (E)-6,6'-(ethene-1,2-diyl)bis(3-cyanobenzenesulfonate) |
| B-3 | | potassium (E)-6,6'-(ethene-1,2-diyl)bis(3-iodobenzenesulfonate) |

The compounds of Table 1 were named using ChemDraw® Professional 15.0 (PerkinElmer).

According to an embodiment, $R^A$ and/or $R^B$ is not thiocyanate. According to an embodiment, $R^A$ and/or $R^B$ is not nitro.

According to an R is not methyl. According to an embodiment, R is not ethyl.

Reference to a compound according to the invention encompasses any enantiomers, solvates (e.g., hydrates), polymorphs (e.g., crystallin forms), multi-component complexes and pharmaceutically acceptable salts thereof. Reference to a compound according to the invention further encompasses any prodrug thereof.

Reference to a compound according to the invention further encompasses any pharmaceutically acceptable salts thereof. Pharmaceutically acceptable salts include the acid addition and base salts thereof. Suitable acid addition salts are formed from acids which form non-toxic salts. Examples include the acetate, adipate, aspartate, benzoate, besylate, bicarbonate/carbonate, bisulphate/sulphate, borate, camsylate, citrate, cyclamate, edisylate, esylate, formate, fumarate, gluceptate, gluconate, glucuronate, hexafluorophosphate, hibenzate, hydrochloride/chloride, hydrobromide/bromide, hydroiodide/iodide, isethionate, lactate, malate, maleate, malonate, mesylate, methylsulphate, naphthylate, 2-napsylate, nicotinate, nitrate, orotate, oxalate, palmitate, pamoate, phosphate/hydrogen, phosphate/dihydrogen, phosphate, pyroglutamate, saccharate, stearate, succinate, tannate, tartrate, tosylate, trifluoroacetate and xinofoate salts. Suitable base salts are formed from bases which form non-toxic salts. Examples include the aluminium, arginine, benzathine, calcium, choline, diethylamine, diolamine, glycine, lysine, magnesium, meglumine, olamine, potassium, sodium, tromethamine, 2-(diethylamino)ethanol, ethanolamine, morpholine, 4-(2-hydroxyethyl)morpholine and zinc salts. Hemi-salts of acids and bases may also be formed, e.g., hemi-sulphate and hemi-calcium salts. When the compound contains an acidic group as well as a basic group it may also form internal salts. When the compound contains a hydrogen-donating heteroatom (e.g., NH), a pharmaceutically acceptable salt thereof includes also salts and/or isomers formed by transfer of said hydrogen atom to a basic group or atom within the molecule. These salts may be prepared by standard procedures, e.g., by reacting a free acid with a suitable organic or inorganic base.

Compounds with no sulfonate functions, which are not part of the present invention, are presented in Table 2 below:

TABLE 2

| # | Formula | Name |
|---|---------|------|
| X-1 | | (E)-N,N'-(ethene-1,2-diylbis(4,1-phenylene))diacetamide |
| X-2 | | diphenyl (ethene-1,2-diylbis(4,1-phenylene))(E)-dicarbamate |
| X-3 | | (E)-N,N'-(ethene-1,2-diylbis(4,1-phenylene))dibenzenesulfonamide |
| X-4 | | (E)-1,2-bis(4-azidophenyl)ethene |

The compounds of Table 2 were named using ChemDraw© Professional 15.0 (PerkinElmer). The compounds of Table 2 are used for comparison purposes in the "EXAMPLES" section below. They are not part of the present invention.

Synthesis

The compound according to the invention as described hereabove can be manufactured by any synthetic method known in the art.

According to one embodiment, the compound is manufactured starting from sodium (E)-6,6'-(ethene-1,2-diyl)bis(3-aminobenzenesulfonate) (DADS):

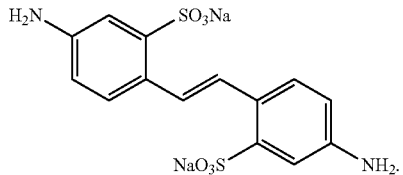

In one embodiment, the compound is manufactured by reaction of DADS with an acid halide or an anhydride halide such as for example an acid chloride or an anhydride chloride. In one embodiment, the compound is manufactured by reaction of DADS with a halo-formate such as for example a chloroformate. In one embodiment, the compound is manufactured by reaction of DADS with a sulfonyl halide such as for example a sulfonyl chloride. In one specific embodiment, the reaction is carried out in basic medium such as for example in presence of $Na_2CO_3$ or N,N-diisopropylethylamine (DIEA). In one specific embodiment, the reaction is carried out in a solvent, such as for example water/dioxane mixture, dimethylsulfoxide (DMF) or dichloromethane ($CH_2Cl_2$). In one specific embodiment, a catalyst may be present such as for example tetrabutylammonium chloride. In one specific embodiment, the reaction is carried out at room temperature or at 80° C.

These embodiments are illustrated by Scheme 1 below.

Scheme 1

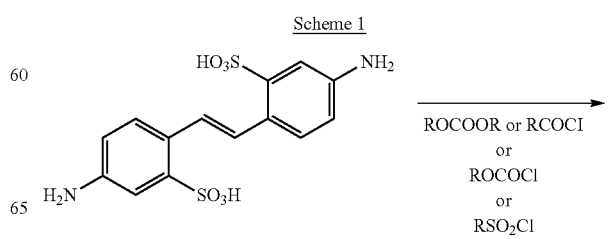

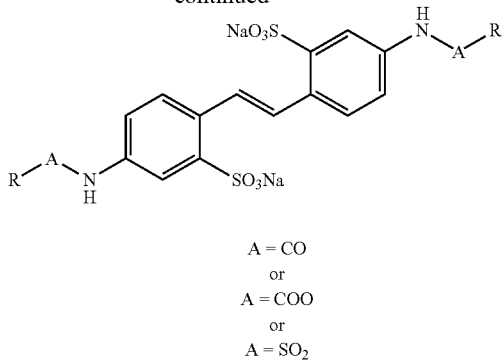

A = CO
or
A = COO
or
A = SO$_2$

In one embodiment, the compound is manufactured starting from DADS by substitution of the aromatic amino groups via the preparation of a double diazonium salt followed by its displacement with a nucleophile (Sandmeyer reaction) the nucleophile being for example $N_3^-$, $CN^-$ or $I^-$.

In one specific embodiment, the preparation of the double diazonium salt is carried out in presence of $Na_2NO_2$ and acetic acid (AcOH). In one specific embodiment, the nucleophile is a sodium or potassium salt. In one specific embodiment, the displacement step is carried out in the presence of a catalyst, e.g. a copper (I) or (II) catalyst such as for example copper iodide (CuI). In one specific embodiment, the first and/or the second reaction steps is/are carried out in a solvent, such as for example water. In one specific embodiment, the first and/or the second reaction steps is/are carried out is carried out at room temperature.

Compositions

The invention also relates to a composition comprising a compound according to the invention as described hereabove.

According to an embodiment, the composition further comprises at least another active ingredient, i.e., comprises a compound according to the invention and another different active ingredient. In one embodiment, the active ingredient is an antineoplastic drug, i.e., a compound active in treating a proliferative disease. In one specific embodiment, the active ingredient is selected from alkylating agents, antimetabolites, anti-microtubule agent, topoisomerase inhibitors and cytotoxic antibiotics. Examples of antineoplastic drugs are listed in *Actualité Pharmaceutiques*, October 1992 (No. 302, pp. 41-43), hereby incorporated by reference. In one further specific embodiment, the active ingredient is selected from alkylating agents selected from nitrogen mustards, nitrosoureas, tetrazines, aziridines, cisplatin and cisplatin derivatives (e.g., carboplatin and oxaliplatin) and non-classical alkylating agents such as procarbazine and hexamethylmelamine. Examples of antineoplastic drugs include cisplatin or derivatives thereof; inhibitors of topoisomerase such as etoposide or topotecan; or tyrosine kinase receptors such as erlotinib or imatinib.

According to an embodiment, the composition further comprises a pharmaceutically acceptable excipient. In one embodiment, the composition is a pharmaceutical composition. In one embodiment, the composition is a medicament.

Kit

The invention also relates to a kit comprising a compound or a composition according to the invention as described hereabove.

According to one embodiment, the kit includes at least one pharmaceutical composition according to the invention and at least another pharmaceutical composition comprising another active ingredient.

According to one embodiment, the kit includes a plurality of pharmaceutical compositions according to the invention, e.g., a plurality of single doses for monthly, weekly or daily administration.

Uses and Methods

The invention also relates to the use of a compound or a composition according to the invention as described hereabove for inhibiting DNA repair, e.g., for inhibiting double-strand break repair. The invention also relates to a method for inhibiting DNA repair (e.g., double-strand break repair) in a subject in need thereof, comprising a step of administration of a compound or a composition according to the invention as described hereabove to the subject.

According to an embodiment, inhibition of double-strand break repair comprises inhibition of RAD51 protein. Inhibition of RAD51 protein includes any reduction of the presence of RAD51 protein such as for example prevention of RAD51 protein synthesis and/or prevention of RAD51 protein folding. Inhibition of RAD51 protein also includes any reduction of RAD51 protein biological activity, such as for example prevention of the formation of RAD51 protein nucleofilament, RAD51 protein binding with DNA and/or catalytic activity of RAD51 protein.

The invention also relates to a compound or a composition according to the invention as described hereabove for use as a medicament. According to one embodiment, the invention relates to the compound or the composition for use in the treatment of a proliferative disease. According to one embodiment, the invention relates to the compound or the composition for use in the treatment of cancer.

The invention also relates to a method of treatment of a disease in a subject in need thereof comprising a step of administration to the subject of a compound or a composition according to the invention as described hereabove. According to one embodiment, the disease is a proliferative disease.

The invention also relates to the use of a compound or a composition according to the invention as described hereabove in the manufacture of a medicament. According to one embodiment, the medicament is for treating a proliferative disease.

In one embodiment, the proliferative disease is cancer. In a specific embodiment, the cancer is selected from breast cancer, glioblastoma and multiple myeloma. In one embodiment, the treatment is first, second or third line cancer treatment.

According to one embodiment, the compound or the composition is simultaneously, sequentially or separately administered with at least another active ingredient to the subject in need thereof. In one embodiment, the other active ingredient is administrated by simultaneous administration with the compound or the composition. In one embodiment, the other active ingredient is administrated by sequential administration with the compound or the composition. In one embodiment, the other active ingredient is administrated by separate administration with the compound or the composition.

According to one embodiment, the compound is not for use in the treatment of viral diseases. In one embodiment, the compound is not for use in the treatment of HSV, HIV or CMV. According to one embodiment, the compound is not for use in the treatment of inflammatory diseases. In one embodiment, the compound is not for use in the treatment of inflammatory skin diseases. According to one embodiment, the compound is not for use in the treatment of autoimmune diseases. According to one embodiment, the compound is not for use in contraception.

According to one embodiment, the compound is not a follicle stimulating hormone (FSH) antagonist. According to one embodiment, the compound is not a chloride channel or transporter compound (CLCs).

EXAMPLES

The present invention is further illustrated by the following examples.

Example 1: Synthesis of Stilbene Compounds

Materials and Methods

Materials

Sodium (E)-6,6'-(ethene-1,2-diyl)bis(3-aminobenzenesulfonate) (DADS) was purchased from Alfa Aesar (4,4'-Diaminostilbene-2,2'-disulfonic acid, CAS 81-11-8). Others reactants including 4,4'-diamino stilbene dihydrochloride (CAS 54760-75-7) were purchased from Sigma Aldrich (Bethesda, US). All solvents used were reagent grade. Thin layer chromatography (TLC) was performed on silica-covered aluminium sheets (Kieselgel $60F_{254}$, MERCK).

General Methods

Eluted TLC was revealed using UV radiation ($\lambda$=254 nm), or molybdate solution. NMR spectra were recorded on a BRUKER AC300 (300 MHz for $^1$H and 75 MHz for $^{13}$C) or on a BRUKER 400 (400 MHz for $^1$H and 100 MHz for $^{13}$C) at room temperature, on samples dissolved in an appropriate deuterated solvent. References of tetramethylsilane (TMS) for $^1$H and deuterated solvent signal for $^{13}$C were used. Chemical displacement values (b) are expressed in parts per million (ppm) and coupling constants (J) in Hertz (Hz). Clearly identified proton and carbon were specified. Infrared spectrometry analyses were recorded on an IRTF Bruker Tensor 27, Vector 22. Low-resolution mass spectra (MS in Da unit) were recorded in the CEISAM laboratory on a Thermo-Finnigan DSQII quadripolar at 70 eV (CI with $NH_3$ gas) or on a Waters Xevo G2-XS QTOF. High-Resolution Mass Spectrometry (HRMS in Da unit) analyses were recorded on an LC-Q-TOF (Synapt-G2 HDMS, Waters) in the IRS-UN center (Mass Spectrometry platform, Nantes).

Synthetic Methods

General Synthetic Procedure 1:
To a suspension of DADS (1 mmol, 0.37 g) in a mixture of water/dioxane (ratio 10:2) was added $Na_2CO_3$ (5 eq., 5 mmol). The solution became clear and yellow and anhydride (4 mmol) was added with a catalytic amount of tetrabutylammonium chloride (0.1 eq). After stirring during 2 h to 18 h, a precipitate was formed. It was filtered, washed with $Et_2O$ to give the expected pure compound as observed by NMR analysis. A second precipitation step (DMSO:$Et_2O$) could be done for purity optimization.
General Synthetic Procedure 2:
To a solution of DADS (1 mmol, 0.37 g) in dimethylsulfoxide (DMF) was added N,N-diisopropylamine (DIEA) (5 eq). Acid chloride (4 eq) was added and the reaction was heated to 80° C. overnight. After cooling to room temperature, methanol was added until a precipitate was formed. This was filtered and washed with $Et_2O$. The precipitate was then dissolved in DMSO and a water solution of $Na_2CO_3$ was added to obtain the expected sodium salt, after precipitation with $Et_2O$.
General Synthetic Procedure 3:
To a suspension of DADS (1 mmol, 0.37 g) in a mixture of water/dioxane (ratio 10:2) was added $Na_2CO_3$ (5 eq., 5 mmol). The solution became clear and yellow and chloroformate reagent (2.5 eq) was added. After stirring overnight, a precipitate was formed. It was filtered, washed with $Et_2O$ to give the expected pure compound as observed by NMR analysis. A second precipitation step (DMSO:$Et_2O$) could be done for purity optimization.
General Synthetic Procedure 4:
To a suspension of DADS (1 mmol, 0.37 g) in a mixture of water/dioxane (ratio 10:2) was added $Na_2CO_3$ (5 eq., 5 mmol). The solution became clear and yellow and sulfonyl chloride reagent (2.5 eq) was added. After stirring overnight, a precipitate was formed. It was filtered, washed with $Et_2O$ to give the expected pure compound as observed by NMR analysis. A second precipitation step (DMSO:$Et_2O$) could be done for purity optimization.
General Synthetic Procedure 5:
To a solution of 4,4'-diamino stilbene dihydrochloride (1 mmol, 0.28 g) in $CH_2Cl_2$ (10 mL) was added N,N-diisopropylethylamine (DIEA) (5 eq). The solution became clear and brown and the chloride reagent (2.5 eq) was added. After stirring overnight, a precipitate was formed. It was filtered, washed with $Et_2O$ to give the expected pure compound as observed by NMR analysis. A second precipitation step (DMSO:$Et_2O$) could be done for purity optimization.
General Synthetic Procedure 6:
To a suspension of DADS (1 mmol, 0.37 g) in water (6 mL) is added $Na_2NO_2$ (0.14 g, 2.2 eq) in solution in water (2 mL) and then acetic acid (5 eq) in solution in water (2 mL). After stirring during 45 min, sodium or potassium salt was added (2 eq to 4 eq in 2 mL of water) in the presence or not of a catalytic amount of Cu(I) (0.2 eq). After stirring during 4 h to 3 days, MeOH and $Et_2O$ were added to obtain a precipitate. It was filtered, washed with $Et_2O$ to give the expected pure compound as observed by NMR analysis. A second precipitation step (DMSO:$Et_2O$) could be done for purity optimization.

Results

Disulfonate stilbene compounds presented on Table 1 above and comparative un-sulfonated stilbene compounds presented on Table 2 above were synthetized by the general synthetic procedures 1-5 described above.

Sodium (E)-6,6'-(ethene-1,2-diyl)bis(3-acetamidobenzenesulfonate) (A-1) was prepared from DADS and acetic anhydride following general synthetic procedure 1. After purification by precipitation it was obtained pure with 62% yield. $^1$H NMR (300 MHz, DMSO-$d_6$): δ ppm 10.03 (s, 2H, 2×NH), 7.96 (s, 2H, CH=CH), 7.94 (d, 2H, 2×Har), 7.68 (dd, 2H, 2×Har), 7.52 (d, 2H, 2×Har), 2.03 (s, 6H, 2×$CH_3$). $^{13}$C NMR (75 MHz, DMSO-$d_6$): δ ppm 168.08 (2×CO), 145.69 (2×$C_{IV}$ar), 137.29 (2×$C_{IV}$ar), 129.88 (2×$C_{IV}$ar), 125.98 (CH=CH), 125.57 (2×CHar), 118.99 (2×CHar), 117.74 (2×CHar), 23.90 (2×$CH_3$). MS (ESI$^+$) m/z: [M+Na]+=521.0, MS (ESI$^-$) m/z: [M−Na]$^-$=475.0. HRMS (ESI$^+$): cald for [M+Na] $C_{18}H_{16}N_2O_8Na_3S_2$ 521.0041; found 521.0029.

Sodium (E)-6,6'-(ethene-1,2-diyl)bis(3-propionamidobenzenesulfonate)) (A-2) was prepared from DADS and propionic anhydride following general synthetic procedure 1. After purification by precipitation it was obtained with 76% yield. $^1$H NMR (300 MHz, DMSO-$_{d6}$): δ ppm 9.63 (s, 2H, 2×NH), 7.93 (s, 2H, CH=CH), 7.90 (s, 2H, 2×Har), 7.49 (s, 4H, 4×Har), 4.12 (q, 4H, 2×CH$_2$), 1.24 (t, 6H, 2×CH$_3$). $^{13}$C NMR (75 MHz, DMSO-$_{d6}$): δ ppm 153.43 (2×CO), 145.71 (2×C$_{IV}$ar), 137.13 (2×C$_{IV}$ar), 129.40 (2×C$_I$var), 125.88 (CH=CH), 125.68 (2×CHar), 118.39 (2×CHar), 117.22 (2×CHar), 60.04 (2×CH$_2$), 14.50 (2×CH$_3$). MS (ESI$^-$) m/z: [M−Na]$^-$=535.2. HRMS (ESI$^-$): cald for [M−Na]$^-$ C$_{20}$H$_{20}$N$_2$O$_{10}$NaS$_2$ 535.0457; found 535.0443.

Sodium (E)-6,6'-(ethene-1,2-diyl)bis(3-benzamidobenzenesulfonate) (A-3) was prepared from DADS and benzoic anhydride following general synthetic procedure 1. After purification by precipitation it was obtained with 70% yield. $^1$H NMR (300 MHz, DMSO-$_{d6}$): δ ppm 8.11 (s, 2H, CH=CH), 8.09 (s, 2H, 2×Har), 7.96 (d, 2H, 2×Har), 7.69 (d, 2H, 2×Har), 7.33 (m, 10H, 10×Har). $^{13}$C NMR (75 MHz, DMSO-$_{d6}$): δ ppm 154.04 (2×C$_{IV}$ar'), 152.35 (2×CO), 144.27 (2×C$_{IV}$ar), 138.64 (2×C$_{IV}$ar), 132.13 (2×C$_{IV}$ar), 130.45 (4×CHar'), 128.67 (2×CHar), 127.99 (CH=CH), 126.64 (2×CHar), 122.92 (4×CHar), 121.57 (2×CHar), 119.01 (2×CHar). MS (ESI$^+$) m/z: [M+Na]+=676.9. HRMS (ESI$^+$): cald for [M+Na] C$_{28}$H$_{20}$N$_2$O$_{10}$Na$_3$S$_2$ 677.0252; found 677.0262.

Sodium (E)-6,6'-(ethene-1,2-diyl)bis(3-(4-methoxybenzamido)benzenesulfonate) (A-4) was prepared from DADS and 4-methoxybenzoyl chloride following general synthetic procedure 2. After purification by precipitation it was obtained with 44% yield. $^1$H NMR (300 MHz, CD$_3$OD): a ppm 10.21 (s, 2H, 2×NH), 8.18 (d, 2H, 2×Har), 8.05 (s, 2H, CH=CH), 8.02 (d, 4H, 4×Har), 7.88 (dd, 2H, 2×Har), 7.58 (d, 2H, 2×Har), 7.05 (d, 4H, 4×Har), 3.84 (s, 6H, 2×CH$_3$). $^{13}$C NMR (75 MHz, CD$_3$OD): a ppm 164.57 (2×CO), 161.80 (2×C$_{IV}$ar'), 145.66 (2×C$_{IV}$ar), 137.37 (2×C$_{IV}$ar), 130.27 (2×C$_{IV}$ar), 129.60 (4×CHar), 126.77 (2×C$_{IV}$ar), 126.14 (CH=CH), 125.41 (2×CHar), 120.35 (2×CHar), 119.18 (2×CHar), 113.48 (4×CHar), 55.35 (2×OMe). MS (ESI$^-$) m/z: [M−Na]$^-$=659.1. HRMS (ESI$^-$): cald for [M−2Na]$^2$−C$_{30}$H$_{25}$N$_2$O$_{10}$S$_2$ 637.0951; found 637.0932. Cald for [M−Na]$^-$ C$_{30}$H$_{24}$N$_2$O$_{10}$NaS$_2$ 659.0770; found 659.0778.

Sodium (E)-6,6'-(ethene-1,2-diyl)bis(3-(4-nitrobenzamido)benzenesulfonate) (A-5) was prepared from DADS and 4-nitrobenzoyl chloride following general synthetic procedure 2. After purification by precipitation it was obtained with 70% yield. $^1$H NMR (300 MHz, DMSO-$_{d6}$): δ ppm 10.70 (s, 2H, 2×NH), 8.36 (m, 4H, 4×Har), 8.24 (m, 6H, 6×Har), 8.08 (s, 2H, CH=CH), 7.91 (dd, 2H, 2×Har), 7.63 (d, 2H, 2×Har). $^{13}$C NMR (75 MHz, DMSO-$_{d6}$): δ ppm 163.54 (2×CO), 149.06 (2×C$_{IV}$ar), 145.86 (2×C$_{IV}$ar), 140.41 (2×C$_{IV}$ar), 136.78 (2×C$_{IV}$ar), 130.92 (2×C$_{IV}$ar), 129.23 (4×CHar), 126.42 (2×CHar), 125.58 (CH=CH), 123.41 (4×CHar), 120.44 (2×CHar), 119.32 (2×CHar). MS (ESI$^+$) m/z: [M+Na]+=734.9, MS (ESI$^-$) m/z: [M−Na]$^-$=688.9. HRMS (ESI$^+$): cald for [M+Na]+C$_{28}$H$_{18}$N$_4$O$_{12}$Na$_3$S$_2$ 735.0056; found 735.0057.

Sodium (E)-6,6'-(ethene-1,2-diyl)bis(3-((ethoxycarbonyl)amino)benzenesulfonate) (C-1) was prepared from DADS and ethyl chloroformate following general synthetic procedure 3. After purification by precipitation it was obtained with 66% yield. $^1$H NMR (300 MHz, DMSO-$_{d6}$): δ ppm 9.63 (s, 2H, 2×NH), 7.93 (s, 2H, CH=CH), 7.90 (s, 2H, 2×Har), 7.49 (s, 4H, 4×Har), 4.12 (q, 4H, 2×CH$_2$), 1.24 (t, 6H, 2×CH$_3$). $^{13}$C NMR (75 MHz, DMSO-$_{d6}$): δ ppm 153.43 (2×CO), 145.71 (2×C$_{IV}$ar), 137.13 (2×C$_{IV}$ar), 129.40 (2×C$_I$var), 125.88 (CH=CH), 125.68 (2×CHar), 118.39 (2×CHar), 117.22 (2×CHar), 60.04 (2×CH$_2$), 14.50 (2×CH$_3$). MS (ESI$^-$) m/z: [M−Na]$^-$=535.2. HRMS (ESI$^-$): cald for [M−Na]$^-$ C$_{20}$H$_{20}$N$_2$O$_{10}$NaS$_2$ 535.0457; found 535.0443.

Sodium (E)-6,6'-(ethene-1,2-diyl)bis(3-((isobutoxycarbonyl)amino)benzenesulfonate) (C-2) was prepared from DADS and isobutyl chloroformate following general synthetic procedure 3. After purification by precipitation it was obtained with 67% yield. $^1$H NMR (300 MHz, DMSO-$_{d6}$): δ ppm 9.65 (s, 2H, 2×NH), 7.94 (s, 2H, CH=CH), 7.92 (d, 2H, 2×Har), 7.49 (m, 4H, 4×Har), 3.87 (d, 4H, 2×CH$_2$), 1.92 (m, 2H, 2×CH), 0.94 (d, 12H, 4×CH$_3$). $^{13}$C NMR (75 MHz, DMSO-$_{d6}$): δ ppm 153.58 (2×CO), 145.72 (2×C$_{IV}$ar), 137.169 (2×C$_{IV}$ar), 129.41 (2×C$_{IV}$ar), 125.89 (CH=CH), 125.70 (2×CHar), 118.44 (2×CHar), 117.25 (2×CHar), 70.01 (2×OCH2), 27.55 (2×CH), 18.90 (4×CH$_3$). MS (ESI$^+$) m/z: [M+Na]+=637.1, MS (ESI$^-$) m/z: [M−Na]$^-$=591.0. HRMS (ESI$^+$): cald for [M+Na]+C$_{24}$H$_{28}$N$_2$O$_{10}$Na$_3$S$_2$ 637.0878; found 637.0870.

Sodium (E)-6,6'-(ethene-1,2-diyl)bis(3-((phenoxycarbonyl)amino)benzenesulfonate) (C-3) was prepared from DADS and phenyl chloroformate following general synthetic procedure 3. After purification by precipitation it was obtained with 38% yield. $^1$H NMR (300 MHz, CD$_3$OD): δ ppm 8.11 (s, 2H, CH=CH), 8.09 (s, 2H, 2×Har), 7.96 (d, 2H, 2×Har), 7.69 (dd, 2H, 2×Har), 7.39 (m, 4H, 4×Har), 7.22 (m, 6H, 6×Har). $^{13}$C NMR (75 MHz, CD$_3$OD): δ ppm 154.04 (2×C$_{IV}$ar), 152.35 (2×CO), 144.27 (2×C$_{IV}$ar), 138.64 (2×C$_{IV}$ar), 132.13 (2×C$_{IV}$ar), 130.45 (4×CHar), 128.67 (2×CHar), 127.99 (CH=CH), 126.64 (2×CHar), 122.92 (4×CHar), 121.57 (2×CHar), 119.01 (2×CHar). MS (ESI$^+$) m/z: [M+Na]+=676.9. HRMS (ESI$^+$): cald for [M+Na]$^+$ C$_{28}$H$_{20}$N$_2$O$_{10}$Na$_3$S$_2$ 677.0252; found 677.0262.

Sodium (E)-6,6'-(ethene-1,2-diyl)bis(3-(phenylsulfonamido)benzenesulfonate) (S-1) was prepared from DADS and benzenesulfonyl chloride following general synthetic procedure 4. After purification by precipitation it was obtained with 81% yield. $^1$H NMR (300 MHz, D$_2$O): δ ppm 7.80 (m, 4H, Har), 7.65 (s, 2H, CH=CH), 7.64 (d, 2H, J=8.2 Hz, 2×Har), 7.60-7.48 (m, 6H, Har), 7.43 (d, 2H, J=2.44 Hz, 2×Har), 7.06 (dd, 2H, J=2.44 Hz and 8.6 Hz, 2×Har). $^{13}$C NMR (75 MHz, D$_2$O): δ ppm 144.06 (2×C$_{IV}$), 141.11 (2×C$_{IV}$), 140.19 (2×C$_{IV}$), 132.18 (2×CHar), 129.11 (4×CHar), 127.91 (2×CHar), 127.61 (2×C$_{IV}$), 126.47 (4×CHar), 125.78 (CH=CH), 124.40 (2×CHar), 119.66 (2×CHar). HRMS (ESI$^+$): cald for C$_{26}$H$_{19}$N$_2$O$_{10}$Na$_2$S$_4$ [M−H]$^-$ 692.9718; found 692.9719.

Sodium (E)-6,6'-(ethene-1,2-diyl)bis(3-((4-methylphenyl)sulfonamido)benzenesulfonate) (S-2) was prepared from DADS and para-toluenesulfonyl chloride following general synthetic procedure 4. After purification by precipitation it was obtained with 87% yield. $^1$H NMR (300 MHz, D$_2$O): δ ppm 7.68 (m, 4H, 4×Har), 7.64 (s, 2H, CH=CH), 7.64 (s, 2H, CH=CH), 7.64 (d, 2H, 2×Har), 7.42 (d, 2H, J=2.4 Hz, 2×Har), 7.33 (m, 4H, 4×Har), 7.03 (dd, 2H, J=8.5 Hz and 2.5 Hz, 2×Har), 2.35 (s, 6H, 2×CH$_3$). HRMS (ESI$^-$): cald for C$_{28}$H$_{23}$N$_2$O$_{10}$S$_4$Na$_2$ [M+H]$^-$ 721.0031; found 721.0024.

Sodium (E)-6,6'-(ethene-1,2-diyl)bis(3-(4-nitrophenylsulfonamido)benzenesulfonate) (S-3) was prepared from DADS and 4-nitrobenzenesulfonyl chloride following general synthetic procedure 3. After purification by precipitation it was obtained with 81% yield. $^1$H NMR (300 MHz, D$_2$O): δ ppm 8.32 (dl, 4H, 4×Har), 7.99 (dl, 4H, 4×Har), 7.664 (m, 4H, 2×Har and CH=CH), 7.43 (sl, 2H, 2×Har), 7.05 (dl, 2H, 2×Har). HRMS (ESI⁺): calcd for $C_{26}H_{19}N_4O_{14}S_4Na_2$ [M+H]⁺ 784.9570; found 784.9560.

(E)-N,N'-(ethene-1,2-diylbis(4,1-phenylene))diacetamide (X-1) was prepared from 4,4'-diamino stilbene dihydrochloride and acetyl chloride following general synthetic procedure 5. After purification by precipitation it was obtained with 53% yield. ¹H NMR (300 MHz, DMSO-$d_6$): δ ppm 10.06 (s, 2H, 2×NH), 7.54 (m, 8H, 8×Har), 7.07 (s, 2H, CH=CH), 2.05 (s, 6H, 2×CH₃). ¹³C NMR (75 MHz, DMSO-$d_6$): δ ppm 168.17 (2×CO), 138.58 (2×$C_{IV}$ar), 131.95 (2×$C_{IV}$ar), 126.58 (4×CHar), 126.47 (CH=CH), 118.98 (4×CHar), 23.96 (2×CH₃). MS (ESI⁺) m/z: [M+Na]+=317.1. HRMS (ESI⁺): calcd for [M+Na]⁺ $C_{18}H_{18}N_2O_2Na$ 317.1266; found 317.1278.

Diphenyl (ethene-1,2-diylbis(4,1-phenylene))(E)-dicarbamate (X-2) was prepared from 4,4'-diamino stilbene dihydrochloride and phenyl chloroformate following general synthetic procedure 5. After purification by precipitation it was obtained with 54% yield. ¹H NMR (300 MHz, DMSO-$d_6$): δ ppm 10.33 (s, 2H, NHCO), 7.57-7.42 (m, 10H, Har), 7.30-7.23 (m, 8H, Har), 7.11 (s, 2H, CH=CH). ¹³C NMR (75 MHz, DMSO-$d_6$): δ ppm 151.54 (2×$C_{IV}$), 150.41 (2×$C_{IV}$), 137.81 (2×$C_{IV}$ar), 131.99 (2×$C_{IV}$ar), 129.36 (4×CHar), 126.82 (4×C), 126.52 (4×CHar), 125.39 (2×CHar), 121.89 (4×CHar), 118.48 (4×CHar). HRMS (ESI⁺): calcd for [M+Na]+$C_{28}H_{22}N_2O_4Na$ 473.1472; found 473.1471.

(E)-N,N'-(ethene-1,2-diylbis(4,1-phenylene))dibenzenesulfonamide (X-3) was prepared from 4,4'-diamino stilbene dihydrochloride and phenylsulfonyl chloride following general synthetic procedure 5. After purification by precipitation it was obtained with 41% yield. ¹H NMR (300 MHz, DMSO-$d_6$): δ ppm 10.31 (sl, 2H, NH), 7.76 (dd, 4H, J=8.33 Hz and 1.55 Hz, 2×Har), 7.60-7.54 (m, 6H, 6×Har), 7.38 (d, 4H, J=8.64 Hz, Har stilb), 7.07 (d, 4H, J=8.64 Hz, Har stilb), 6.97 (s, 2H, CH=CH). HRMS (ESI+): calcd for [M+Na]+ $C_{26}H_{22}O_4N_2NaS_2$ 513.0913; found 513.0918.

(E)-1,2-bis(4-azidophenyl)ethene (X-4) was prepared was prepared from 4,4'-diamino stilbene dihydrochloride following general synthetic procedure 6, with NaN₃ (2 eq) and without Cu catalyst. After filtration of the brown precipitate, purification by column chromatography gave two products and the expected (E)-isomer (X-4) was identified. IR (cm-1): $\upsilon_{max}$=2111 and 2081 (N₃). ¹H NMR (300 MHz, DMSO-$d_6$): δ ppm 7.64 (d, 4H, CHar), 7.23 (s, 2H, CH=CH), 7.13 (d, 4H, CHar).

Sodium (E)-6,6'-(ethene-1,2-diyl)bis(3-azidobenzenesulfonate) (B-1) was prepared from DADS following general synthetic procedure 6, with NaN₃ (2 eq) without copper catalyst. After stirring during 3 h30, Na₂CO₃ was added to obtain a pH around 9. After purification by precipitation it was obtained with 80% yield. ¹H NMR (300 MHz, DMSO-$d_6$): δ ppm 8.04 (s, 2H, CH=CH), 7.63 (d, 2H, 2×Har), 7.50 (d, 2H, 2×Har), 7.12 (dd, 2H, 2×Har). ¹³C NMR (75 MHz, DMSO-$d_6$): δ ppm 147.07 (2×$C_{IV}$), 136.99 (2×$C_{IV}$), 131.82 (2×$C_{IV}$), 127.05 (2×CHar), 126.50 (CH=CH), 119.55 (2×CHar), 117.32 (2×CHar). MS (ESI⁻) m/z: [M−Na]⁻=442.9. HRMS (ESI⁻): calcd for [M−Na]⁻ $C_{14}H_8N_6O_6NaS_2$; 442.9844 found 442.9858.

Sodium (E)-6,6'-(ethene-1,2-diyl)bis(3-cyanobenzenesulfonate) (B-2) was prepared from DADS following general synthetic procedure 6, with NaCN (0.2 g) and CuCl (0.05 g) as the catalyst. After purification by precipitation it was obtained with 59% yield as a brown powder. ¹H NMR (300 MHz, DMSO-$d_6$): δ ppm 8.27 (s, 2H, CH=CH), 8.07 (d, 2H, 2×Har), 7.88 (dd, 2H, 2×Har), 7.77 (d, 2H, 2×Har). ¹³C NMR (75 MHz, DMSO-$d_6$): a ppm 146.59 (2×$C_{IV}$), 138.83 (2×$C_{IV}$), 132.64 (2×CHar), 130.51 (2×CHar), 129.50 (2×CH=CH), 126.64 (2×CHar), 118.62 (2×CN), 109.25 (2×$C_{IV}$). MS (ESI⁻) m/z: [M−Na]⁻=411.

Potassium (E)-6,6'-(ethene-1,2-diyl)bis(3-iodobenzenesulfonate) (B-3) was prepared from DADS following general synthetic procedure 6, with KI (5 eq, 0.83 g) and CuI (0.1 eq, 0.02 g) as the catalyst. After purification by precipitation it was obtained with 41% yield as a brown powder. ¹H NMR (300 MHz, D₂O): a ppm 8.23 (d, J=1.4 Hz, 4H, CHar), 7.92 (dd, J=1.4 Hz and J=8.2 Hz, 4H, CHar), 7.84 (s, 2H, CH=CH), 7.61 (d, J=8.3 Hz, CHar (5)). ¹³C NMR (75 MHz, D₂O): a ppm 140.1 (2×$C_{IV}$), 140.65 (2×CHar), 135.52 (2×CHar), 134.07 (2×$C_{IV}$), 128.9 (2×CHar), 127.9 (CH=CH), 92.37 (2×C—I). MS (ESI⁻) m/z: [M−2K+Na]⁻=612.8; [M−2K+H]⁻=590.8; [M−K]⁻=628.8. HRMS (ESI⁻): calcd for [M−K]⁻ $C_{14}H_8O_6N_2K$ 628.7489; found 628.7496.

Example 2: In Vitro Assays—RAD51 Oligomerization by SDS-PAGE Gel (Crosslink)

Materials and Methods

The reaction was performed at room temperature. 2.5 µm HsRad51 was incubated with the indicated concentrations of tested compounds for 10 min in a buffer containing 20 mm sodium phosphate, 50 mm NaCl, 1 mm MgCl 2, and 1 mm ATP. The cross-linking reactions were initiated by the addition of disuccinimidyl suberate (50 µm) and allowed to proceed for 30 min. Reactions were quenched by the addition of Tris-HCl (pH 7.5, final concentration: 50 mm) followed by subsequent incubations for 15 min. The products were then separated by 12% SDS polyacrylamide gel electrophoresis and detected by Western blot with mouse monoclonal anti-Rad51 antibody (NeoMarkers) and anti-mouse Alexa-Fluor 700-conjugated secondary antibody (Molecular Probes, Eugene, OR). The cross-linked dimer was quantified by an Odyssey Infrared Imaging System scanner (Li-Cor Biosciences) (Martinez, S. F. et al., "Targeting human Rad51 by specific DNA aptamers induces inhibition of homologous recombination", *Biochimie*, December 2010, Vol. 92, No. 12, pp. 1832-1838).

Results

The SDS-PAGE electrophoresis after crosslink maintains and immobilizes the RAD51 protein complexes and thus allows visualization of the degree of oligomerization (polymer formation) of the RAD51 protein. The effect of RAD51 protein inhibitors B-1, B-2, B-3, DIDS and X-4 on this key step of RAD51 protein recombinase activity has thus been evaluated. The results are presented on FIG. 1.

These results show that in presence of the disulfonate stilbenes B-1, B-2 and B-3, a significant reduction of the oligomerization state of RAD51 was observed. The oligomeric forms are very strongly diminished with B-2 comprising two cyano groups. This reduction induced by disulfonate stilbenes B-1, B-2 and B-3 is within the same order of magnitude than the reduction observed with reference compound DIDS. It is the Applicant's understanding that DIDS and B-1 to B-3 prevent the oligomerization by acting on the monomer-monomer interfaces of RAD51 protein.

It is noteworthy that contrary to B-1, comparative compound X-4 which does not comprise the sulfonate groups has no effect on RAD51 protein oligomerization. It therefore appears that the two sulfonate groups are essential to the inhibitory properties of RAD51 protein.

Therefore, disulfonate stilbenes according to the invention are potent RAD51 protein inhibitors as evidenced by prevention of RAD51 protein oligomerization.

Example 3: In Vitro Assays—RAD51 Nucleofilament Formation by Interferometry

Materials and Methods

The binding of Rad51 to ssDNA was monitored and quantified by Bio-Layer Interferometry technology using the BLItz platform (FortéBio Inc.). The procedure includes four steps: (1) the baseline in buffer A containing 1×PBS, 10 mM MgCl2 and 0.0075% Tween20 was recorded for 20 s; (2) loading and binding of Rad51 were measured for 40 s using 1.5 µM Rad51 and 1 mM ATP in buffer A; (3) the dissociation of Rad51 from ssDNA was recorded for 20 s in buffer A; (4) the ssDNA biosensor was regenerated using baths of 50 mM NaOH. Except for the step 2, which used 4 µL drop of the protein sample, the steps 1, 3 and 4 used 250 µL solutions in 0.5 mL tube. The measurement parameters were as follows: room temperature measurement and stirring speed of 2200 rpm. To investigate the effect of CSB and analogs to the ssDNA binding of Rad51, the molecule was included in the protein sample of the step 2 at the indicated concentrations and incubated for 5 min before loading on the biosensor. (Normand, A. et al., "Identification and characterization of human Rad51 inhibitors by screening of an existing drug library.", *Biochemical Pharmacology*, October 2014, Vol. 91, No. 3, pp. 293-300).

Results

Figure 2:
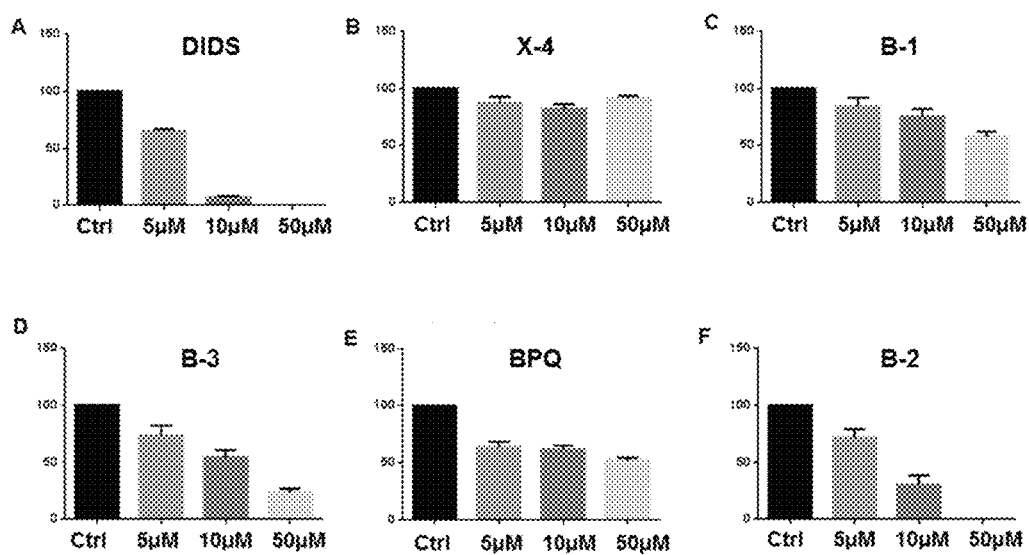
FIG. 2 is a series of histograms each showing on the y-axis the relative binding of RAD51 protein with a single-stranded NDA (%) in presence of one of compounds B-1 to B-3, X-4, DIDS and BPQ with different amounts (μM) of the compounds on the x-axis, as presented in Example 3 below.

A test based on interferometry (Blitz®, Fortebio) allows the measure of the association kinetics of RAD51 protein with a single-stranded DNA immobilized on a biosensor support in the presence or absence of an inhibitor. The effect of compounds B-1, B-2, B-3, BPQ and X-4 on RAD51 nucleofilament formation has been evaluated in presence of increasing doses of inhibitors. The results are presented on FIG. 2.

These results show that disulfonate stilbenes B-1, B-2 and B-3 inhibit the formation of RAD51 protein nucleofilament. The nucleofilament formation is very strongly diminished with B-2 comprising two cyano groups. B-1, B-2 and B-3 activities are comparable to or even better than the one of reference molecule BPQ. B-1, B-2 and B-3 activities are comparable to the one of reference molecule DIDS at low dose (5 µM). B-2 is has the same effect than DIDS at high dose (50 µM).

These results also show that comparative compound X-4 in any amount has no inhibitory effect whatsoever on RAD51 protein.

Therefore, disulfonate stilbenes according to the invention are potent RAD51 protein inhibitors as evidenced by prevention of RAD51 protein nucleofilament formation.

Example 4: In Vitro Assays—DNA Invasion by D-Loop Assays

Materials and Methods

Labeled 100-ssDNA (1 µM) was incubated with 0.5 µM Rad51 in presence or absence of the indicated amounts of the corresponding molecule in 10 µL of standard reaction buffer containing 20 mM Tris-HCl (pH 8), 1 mM ATP, 1 mM DTT, 1 mM CaCl2) at 37° C. for 20 min. The reaction was initiated by adding supercoiled pPB4.3 DNA (200 µM in bp). After incubation of 30 min at 37° C., the reactions were stopped and deproteinized by a stop solution (10 mM Tris-HCl pH 8, 10 mM MgCl2, 1% SDS, and 1 mg/mL proteinase K. The reaction mixtures were further incubated for 15 min at 37° C. After adding 5-fold loading dye (0.05% bromophenol blue, 8% glycerol, 1 mM EDTA), the reaction products were separated by electrophoresis on 1% agarose gel. The electrophoresis was carried out in 0.5×TAE buffer (20 mM Tris, 10 mM acetic acid and 1 mM EDTA) at 100 V for 2 h. The labeled products (100-ssDNA and D-loop) were visualized and quantified by the detection of the IRD-700 dye with the 700 nm infrared fluorescent detection channel of an Odyssey Infrared Imager (LI-COR) (Normand, A. et al., *Biochemical Pharmacology*, October 2014, Vol. 91, No. 3, pp. 293-300).

Results

The "D-loop" in vitro test allows the quantification of the formation of the strand exchange structure (D-loop) and thus the determination of the inhibitory power of a molecule during the strand exchange step of the recombinase mechanism. $IC_{50}$ measuring the RAD51 protein inhibition in presence of compounds A-1 to A-5, B-1 to B-3 B-1 to B-3 and DIDS are then calculated. The results are presented in Table 3 below.

TABLE 3

| Compound | $IC_{50}$ (µM) |
|---|---|
| DIDS | 1 |
| A-3 | >10 |
| A-4 | 6 |
| C-3 | 2 |
| S-1 | 41 |
| S-2 | 29 |
| B-1 | 21 |
| B-2 | 5 |
| B-3 | 34 |

These results show that disulfonate stilbenes A-3, A-4, C-3, S-1, S-2, B-1, B-2 and B-3 have relatively low $IC_{50}$ and thus are potent inhibitors of the formation of the strand exchange structure (D-loop). Disulfonate stilbenes A-4, C-3 and B-2 have very low $IC_{50}$ values within the same order of magnitude the DIDS reference compound and thus are especially efficient in preventing the strand exchange step.

Therefore, disulfonate stilbenes according to the invention are potent RAD51 protein inhibitors as evidenced by DNA invasion.

Example 5: Cellular Assays—Effect on Intracellular Homologous Recombination (HR)

Materials and Methods

After transfection with the pCMV-HA-I-SceI plasmid and incubation for 72 h, the cells were collected in PBS and 50 mM EDTA, pelleted and fixed with 2% paraformaledhyde for 20 min. The percentage of GFP-expressing cells was scored by FACS analysis using Cytoflex (Beckman Coulter). At least 3 independent experiments were performed, and HA-I-SceI expression was verified each time by Western blot with rabbit anti-HA antibody (Abcam).

Results

The recombinant fibroblast line RG37 is used to confirm in vitro results (Examples 2-5) in the cellular context. This cellar line comprises two non-functional GFP cassettes, one of which has a unique cleavage site inducible by transfection of a restriction enzyme. After cleavage, which is equivalent to a double-strand break (DSB) of the DNA, the homologous recombination (HR) leads to the reconstitution of a complete GFP cassette thus making the cell fluorescent. The rate of intracellular HR is then determined by measurement in flow cytometry so as to measure the level of HR in cells after treatment with compounds C-3, B-2 and X-2. The results are presented in FIG. 3.

Figure 3:
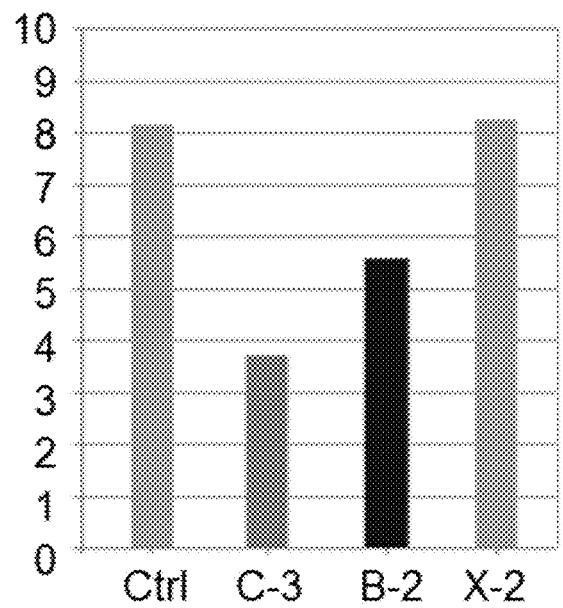
FIG. 3 is a histogram showing on the y-axis the intracellular HR inhibition (%) in presence of one of compounds C-3, B-3 and X-2 as presented in Example 5 below.

These results thus confirmed the results in vitro, since a significant inhibitory effect on HR is obtained with disulfonate stilbenes C-3 and B-2 whereas comparative compound X-2 which does not comprise the sulfonate groups does not lead to any inhibition (FIG. 3).

Therefore, disulfonate stilbenes according to the invention are potent RAD51 protein inhibitors as evidenced by intracellular homologous recombination.

Example 6: Cellular Assays—Sensitizing Effect with an Antineoplastic Drug

Materials and Methods

Clonogenicity tests are carried out against several model cell lines derived from cancer including prostate cancer (DU-145). Cells are exposed to an anti-cancer agent targeting DNA (cisplatin or camptothecin). Damaged cells are counted and seeded in the presence or in the absence of B-2 in triplicate culture plates. After about two weeks of incubation at 37° C. the number of clones formed is counted. Each cell capable of repairing its lesions will then form a clone. After counting, the percentage of survival will be calculated relative to the control condition for which it is considered that there is 100% survival.

Results

The main interest of RAD51 protein inhibitors is the sensitization of chemo-resistant or radio-resistant cancerous cell lines. Clonogenicity evaluation was carried out on the DU-145 cell line treated with cisplatin treatment in the presence or in the absence of disulfonate stilbene B-2 (RAD51 protein inhibitor). The results are presented in FIG. 4 and Table 4 below.

TABLE 4

| Compound | $IC_{50}$ (µM) |
| --- | --- |
| Cisplatin | 33 |
| Cisplatin + B-2 20 µM | 20 |

Figure 4:
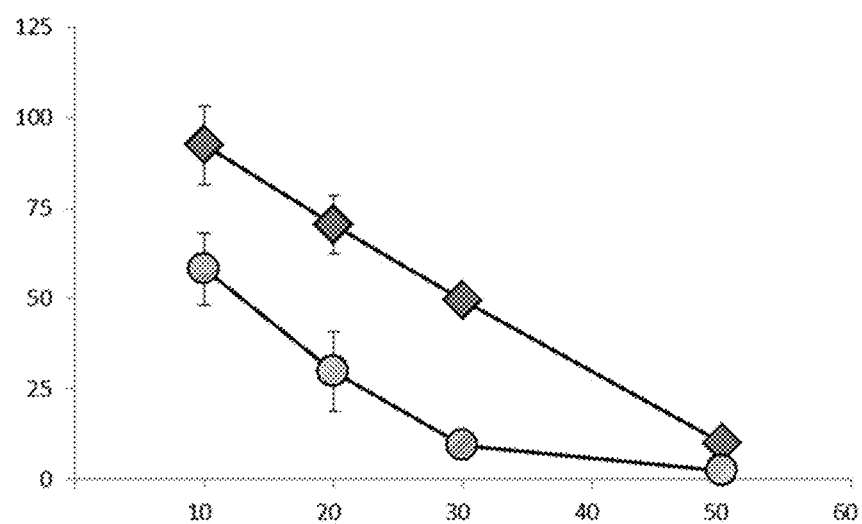
FIG. 4 is a graph showing on the y-axis the cellular survival rate (%) in presence cisplatin alone (above curve with square dots) or in presence of cisplatin together with B-2 compound 20 μM (below curve with circular dots) with different amounts (μM) of cisplatin on the x-axis, as presented in Example 6 below.

These results show that the cellular survival rate in presence of cisplatin alone (above curve with square dots) is higher than in presence of cisplatin together with B-2 compound 20 µM (below curve with circular dots) whatever the amount of cisplatin (FIG. 4). Therefore, B-2 indeed acts as a sensitizing agent against cancerous cell lines in supplement of cisplatin antineoplastic activity. This effect is also evidenced by growth inhibition $IC_{50}$ for cisplatin which decreases of about 40% in presence of B-2 (Table 4).

The same experiment was performed using camptothecin treatment, which is known to induce DNA damages repaired by RAD51-mediated Homologous Recombination.

DU-145 cell line was treated with camptothecin in the presence or in the absence of disulfonate stilbene B-2 (RAD51 protein inhibitor) and the clonogenic cell survival was determined. The results are presented in FIG. 5 and Table 5 below.

TABLE 5

| Compound | $IC_{50}$ (nM) |
| --- | --- |
| camptothecin | 98 |
| camptothecin + B-2 20 µM | 11 |

Figure 5:
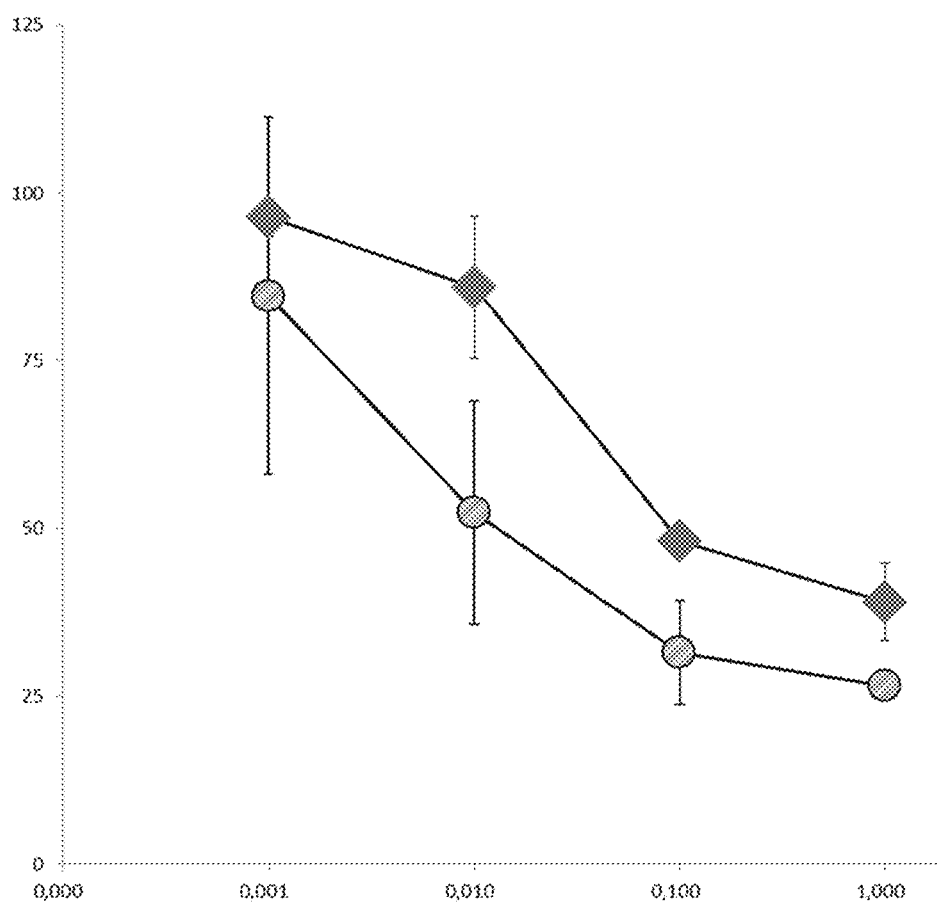
FIG. 5 is a graph showing on the y-axis the cellular survival rate (%) in presence camptothecin alone (above curve with square dots) or in presence of camptothecin together with B-2 compound 20 μM (below curve with circular dots) with different amounts (μM) of camptothecin on the x-axis, as presented in Example 6 below.

These results show that the cellular survival rate in presence of camptothecin alone (above curve with square dots) is higher than in presence of camptothecin together with B-2 compound 20 µM (below curve with circular dots) whatever the amount of camptothecin (FIG. 5). Therefore, B-2 indeed acts as a sensitizing agent against cancerous cell lines in supplement of camptothecin antineoplastic activity. This effect is also evidenced by growth inhibition $IC_{50}$ for camptothecin which decreases of about 90% in presence of B-2 (Table 5).

Therefore, disulfonate stilbenes according to the invention are potent sensitizing agents and are thus useful in the treatment of proliferative diseases.

Example 7: Cellular Assays—Cytotoxicity

Materials and Methods

Prostate cancer cells DU145 (carcinoma) and fibroblast cells were cultured in minimum essential medium (RPMI 1640 medium) supplemented with 10% fetal bovine serum (FBS) and 1% penicillin/streptomycin, and were grown at 37° C. with 5% CO2.

Tested molecules were dissolved and stored in DMSO at 20 mM concentration.

DU145 and fibroblast cells were seeded at 5×103 cells/well in 100 µl of medium in standard 96-well plates. The plates were incubated 24 h at 37° C. at an atmosphere of 5% CO2. Molecule solutions diluted in DMSO were serially diluted by RPMI 1640 medium from 60 µM to 0.02 µM and were added in 100 µl RPMI in quadruplicate.

After 72 h of incubation, 20 µL of 5 mg mL-1 MTT was added to each well according to the manufacturer's instructions. After 2 h of incubation at 37° C., the medium was removed, and 200 µl DMSO was added to each well to dissolve formazan crystals. The absorbance at 540 nm of each well was then monitored using an EnSpire multimode plate reader. Absorbance of each well was expressed as percentage of the control (wells with untreated cells), and the 50% inhibitory concentration ($IC_{50}$) was determined. $IC_{50}$ values are defined as the concentration of drug causing 50% growth inhibition. Results represent the average values of at least three experiments. All data were expressed as the mean values±standard deviation. The $IC_{50}$ values were calculated by linear regression analysis of the concentration-log response curves using the software GraphPad InStat 3.0.

Results

The DU145 prostate cancer cell line was used to evaluate and compare the toxicity of small molecules being the stilbene derivatives of the invention B-1 to B-3 and reference compound BPQ.

Figure 6:
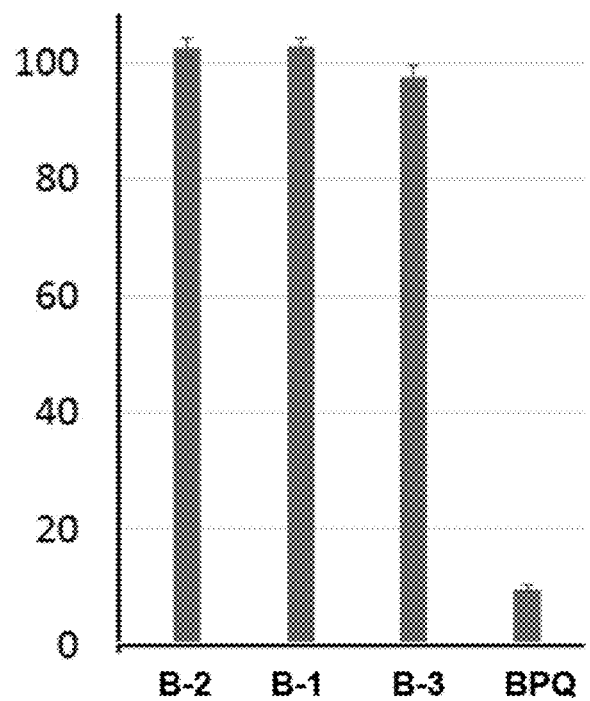
FIG. 6 is a graph showing on the y-axis the cell viability (%) in presence of one of compounds B-1 to B-3 or BPQ as presented in Example 7 below.
Figure 7:
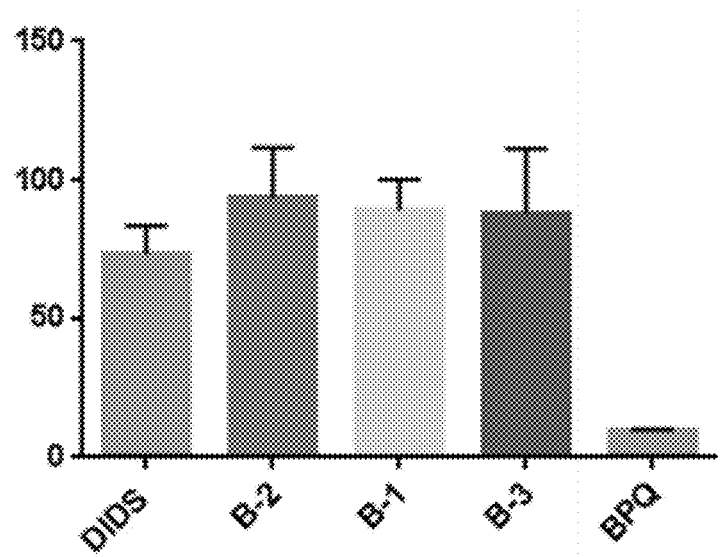
FIG. 7 is a graph showing on the y-axis the survival rate (%) at 50 μM in presence of one of compounds DIDS, B-1 to B-3 or BPQ as presented in Example 7 below.

While compounds B-1 to B-3 have no cytotoxic effect at 50 µM for 3 days on the DU-145 cells, BPQ leads to a high cytotoxicity (low cell viability in the cells in the same concentration with the same incubation time (FIG. 6). Indeed, BPQ causes a 90% mortality of cells whereas the stilbene derivatives of the invention do not affect cell viability (>95% cell viability). The same result has been obtained with fibroblast cells (FIG. 7).

The test carried out with fibroblast cells (FIG. 7) also shows that DIDS has a cytotoxic effect at 50 µM for 3 days, contrary to the stilbene derivatives of the invention.

Example 8: Cellular Assays—Rad51 Foci Quantification

Materials and Methods

DU-145 cells were grown on coverslips (Life Technologies) at a density of 5×10³ cells per well in medium (RPMI) supplemented with 10% fetal bovine serum (Gibco-Invitrogen). Cells were treated with Cisplatin at 30 µM for 1 hour in presence or in absence of RAD51 inhibitor B-2 at 20 µM, and then the medium was replaced with molecule-free medium. After 18 h, cells were washed once in PBS for 5 min and fixed with ethanol absolute for 25 min.

The fixed cells were incubated for 1 h in the PBS buffer containing 1:1000 diluted anti-RAD51 antibody at room temperature. After three 5-min washes in PBS, slides were incubated with PBS solution containing the secondary antibody conjugated with AlexaFluor 555 (dilution 1:0000) for 45 min in dark room. The slides were washed three times in PBS, counterstained and mounted with ProLong Antifade with DAPI (4',6-diamidino-2-phenylindole) (Life Technologies) and coverslips were applied. The slides were viewed with a confocal microscope (Nikon A1RSi, Minato-ku, Tokyo, Japan) and epifluorescence microscope (Nikon Eclipse E800). The images were recorded with NIS Element software (Version 3.6, Nikon, Tokyo, Japan). The quantification of RAD51 foci was processed with a program derived from Fiji-ImageJ software (NIH, Bethesda, Maryland, USA).

Results

The DU145 prostate cancer cell line was used to evaluate the RAD51 foci level after Cisplatin treatment in presence or in absence of B-2.

The treatment with Cisplatin alone induces a high level of RAD51 foci, whereas this level is decreased when the treatment is associated with B-2 20 µM. After the quantification of the number of RAD51 foci per cell, the number of cells containing more than 20 RAD51 foci was determined.

Figure 8:
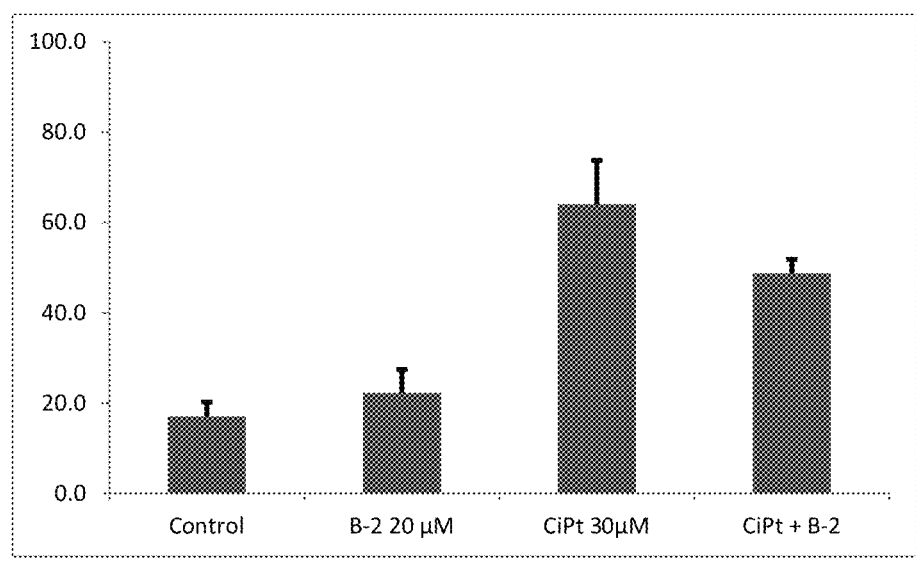
FIG. 8 is a histogram showing on the y-axis the quantification of cell (%) containing more than 20 Rad51 foci per nucleus after a treatment with compound B-2 20 μM, cisplatin 30 μM or compound B-2 20 μM+cisplatin 30 μM as presented in Example 8 below.

The histogram graph in FIG. 8 confirms that the level of RAD51 foci mediated by cisplatin 30 µM is decreased with B-2 (about 20%). This result shows that B-2 is able to decrease the RAD51 foci formation after Cisplatin-mediated DNA damages.

The invention claimed is:

1. A method of treatment of a cancer in a subject in need thereof, wherein the method comprises a step of administration to the subject of a compound of Formula (I)

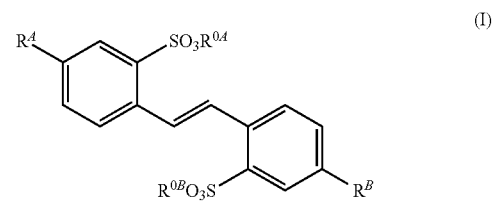

wherein:
$R^{OA}$ and $R^{OB}$ are independently selected from the group consisting of hydrogen, lithium, sodium, and potassium; and
$R^A$ and $R^B$ are identical and selected from the group consisting of —NH—COOR, azido, cyano, and halide;
wherein each R is independently selected from the group consisting of $(C_1$-$C_4)$-alkyl and phenyl;
wherein the phenyl is optionally substituted by one or two substituent(s) independently selected from the group consisting of $(C_1$-$C_3)$-alkyl, $(C_1$-$C_3)$-alkoxy, and nitro;
or a pharmaceutically acceptable salt thereof.

2. The method according to claim 1, wherein the phenyl is optionally substituted by one or two substituent(s) independently selected from the group consisting of methyl, methoxy, and nitro.

3. The method according to claim 1, wherein $R^A$ and $R^B$ are —NH—COOR, wherein each R is independently selected from the group consisting of $(C_1$-$C_4)$-alkyl and phenyl; wherein the phenyl is optionally substituted by one or two substituent(s) independently selected from the group consisting of $(C_1$-$C_3)$-alkyl, $(C_1$-$C_3)$-alkoxy, and nitro.

4. The method according to claim 1, wherein $R^A$ and $R^B$ are selected from azido, cyano, and halide.

5. The method according to claim 1, wherein the halide is iodine.

6. The method according to claim 1, wherein both $R^{OA}$ and $R^{OB}$ are sodium or wherein both $R^{OA}$ and $R^{OB}$ are potassium.

7. The method according to claim 1, wherein the compound of Formula (I) is selected from:

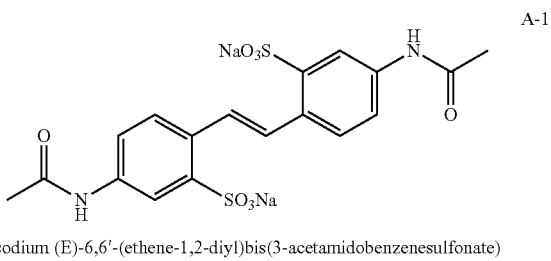

sodium (E)-6,6'-(ethene-1,2-diyl)bis(3-acetamidobenzenesulfonate)

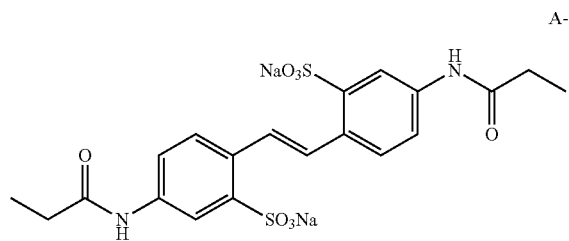

sodium (E)-6,6'-(ethene-1,2-diyl)bis(3-propionamidobenzenesulfonate)  A-2

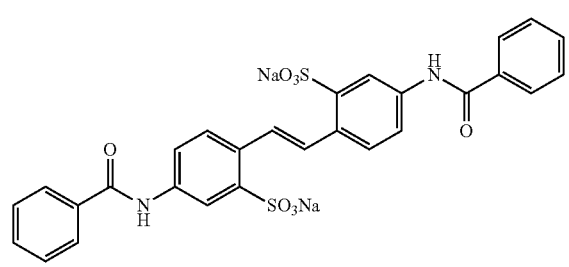

sodium (E)-6,6'-(ethene-1,2-diyl)bis(3-benzamidobenzenesulfonate)  A-3

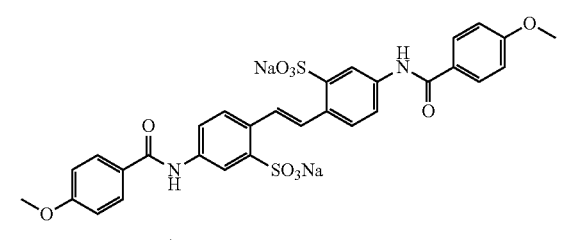

sodium (E)-6,6'-(ethene-1,2-diyl)bis(3-(4-methoxybenzamido)benzenesulfonate  A-4

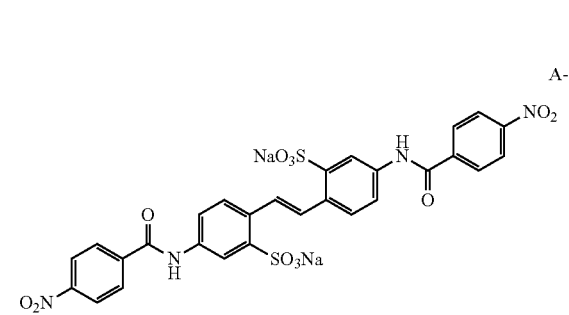

sodium (E)-6,6'-(ethene-1,2-diyl)bis(3-(4-nitrobenzamido)benzenesulfonate  A-5

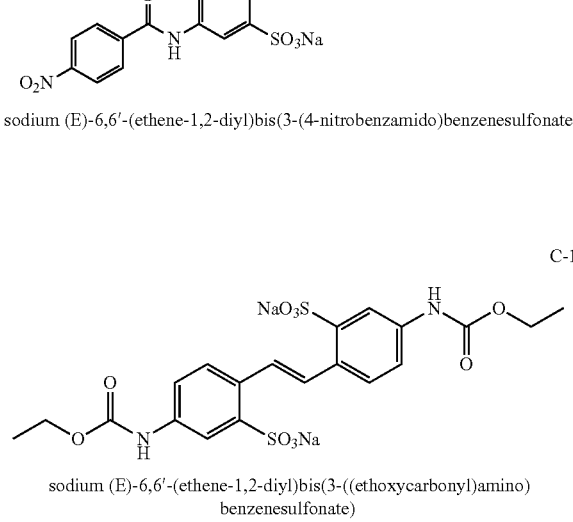

sodium (E)-6,6'-(ethene-1,2-diyl)bis(3-((ethoxycarbonyl)amino)benzenesulfonate)  C-1

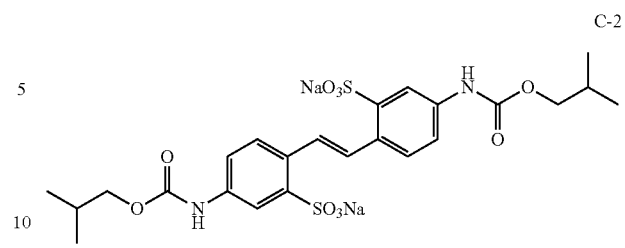

sodium (E)-6,6'-(ethene-1,2-diyl)bis(3-((isobutoxycarbonyl)amino)benzenesulfonate)  C-2

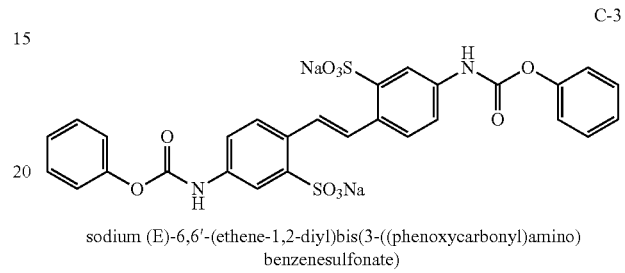

sodium (E)-6,6'-(ethene-1,2-diyl)bis(3-((phenoxycarbonyl)amino)benzenesulfonate)  C-3

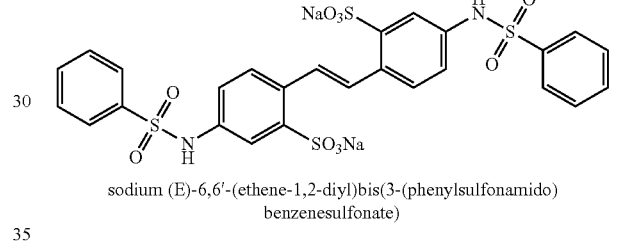

sodium (E)-6,6'-(ethene-1,2-diyl)bis(3-(phenylsulfonamido)benzenesulfonate)  S-1

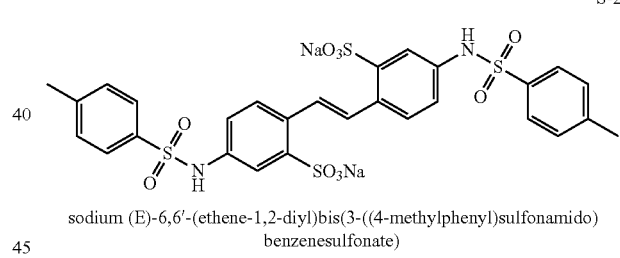

sodium (E)-6,6'-(ethene-1,2-diyl)bis(3-((4-methylphenyl)sulfonamido)benzenesulfonate)  S-2

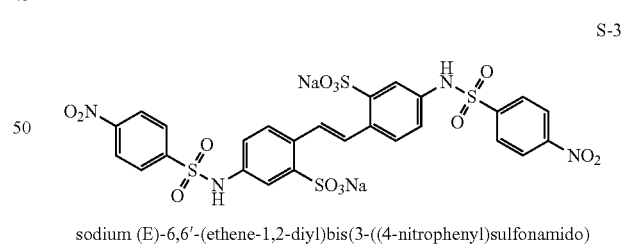

sodium (E)-6,6'-(ethene-1,2-diyl)bis(3-((4-nitrophenyl)sulfonamido)benzenesulfonate)  S-3

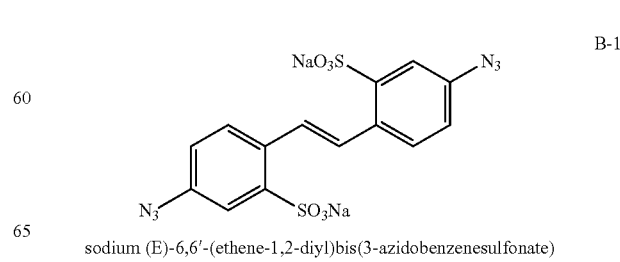

sodium (E)-6,6'-(ethene-1,2-diyl)bis(3-azidobenzenesulfonate)  B-1

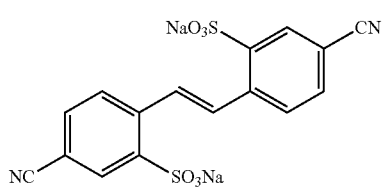

sodium (E)-6,6'-(ethene-1,2-diyl)bis(3-cyanobenzenesulfonate)

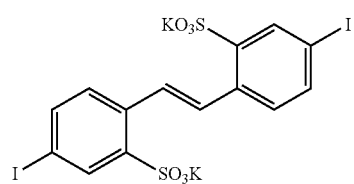

Potassium (E)-6,6'-(ethene-1,2-diyl)bis(3-iodobenzenesulfonate)

and pharmaceutically acceptable salts thereof.

8. The method according to claim 1, wherein said cancer is breast cancer, glioblastoma, or multiple myeloma.

9. The method according to claim 1, comprising a step of administration to the subject of a composition, wherein the composition comprises the compound of Formula (I) and a pharmaceutically acceptable excipient.

10. The method according to claim 9, wherein the composition further comprises at least another active ingredient.

11. The method according to claim 10, wherein the at least another active ingredient is an antineoplastic active ingredient.

* * * * *

UNITED STATES PATENT AND TRADEMARK OFFICE
CERTIFICATE OF CORRECTION

PATENT NO. : 12,233,041 B2
APPLICATION NO. : 17/295231
DATED : February 25, 2025
INVENTOR(S) : Fabrice Fleury et al.

Page 1 of 1

It is certified that error appears in the above-identified patent and that said Letters Patent is hereby corrected as shown below:

In the Claims

Column 34, Claim 7, Lines 55-66, please remove the Chemical Formula.
Column 35, Claim 7, Lines 1-52, please remove the four Chemical Formulas.
Column 36, Claim 7, Lines 25-55, please remove the three Chemical Formulas.

Signed and Sealed this
Thirteenth Day of May, 2025

Coke Morgan Stewart
*Acting Director of the United States Patent and Trademark Office*